(12) United States Patent
DeVico et al.

(10) Patent No.: US 6,548,631 B1
(45) Date of Patent: Apr. 15, 2003

(54) MACROPHAGE DERIVED CHEMOKINE (MDC) AS AN ANTI-VIRAL AGENT FOR THE TREATMENT AND PREVENTION OF LENTIVIRUS INFECTION

(75) Inventors: Anthony L. DeVico, Alexandria, VA (US); Ranajit Pal, Gaithersburg, MD (US); Robert C. Gallo, Bethesda, MD (US); Phillip D. Markham, Rockville, MD (US); Alfredo Garzino-Demo, Washington, DC (US)

(73) Assignee: bioMérieux, Inc., Hazelwood, MO (US)

( * ) Notice: Subject to any disclaimer, the term of this patent is extended or adjusted under 35 U.S.C. 154(b) by 0 days.

(21) Appl. No.: 08/931,764

(22) Filed: Sep. 16, 1997

(51) Int. Cl.[7] .................................................. C07K 7/00
(52) U.S. Cl. ........................ 530/300; 530/351; 435/69.5
(58) Field of Search .............................. 435/5; 530/300, 530/350

(56) References Cited

U.S. PATENT DOCUMENTS

| 5,141,867 A | 8/1992 | Ivanoff et al. | |
| 5,688,927 A | * 11/1997 | Godiska et al. | 530/388.23 |

FOREIGN PATENT DOCUMENTS

| WO | WO 90/07119 | 6/1990 |
| WO | WO 91/09872 | 7/1991 |
| WO | WO 92/22654 | 12/1992 |
| WO | WO 93/03735 | 3/1993 |
| WO | WO 96/40923 | 12/1996 |
| WO | WO 97 39521 A | 12/1996 |
| WO | WO 97 19696 A | 6/1997 |
| WO | WO 97 25350 A | 7/1997 |
| WO | WO 98 24907 A | 6/1998 |

OTHER PUBLICATIONS

Means, G.E., et al., 1990, "Chemical Modifications of Proteins: History and Applications.", Bioconjug. Chem. 1(1):10–20.*

Brinkley, M., 1990, "A Brief Survey of Methods for Preparing Protein Conjugates with Dyes, Haptens, and Cross–linking Reagents.", Bioconjug. Chem. 1(1):59–70.*

Rice, W.G., et al., 1995, "Discovery and in Vitro Development of AIDS Antiviral Drugs as Biopharmaceuticals.", Adv. Pharmacol. 33:389–438.*

Gait, M.J., et al., 1995, "Progress in anti–HIV structure–based design.", TIBTECH 13:430–438.*

Cocchi, F. et al. Role of Beta–Chemokines in Suppressing HIV Replication Science, vol. 274, No. 5291, Nov. 22, 1996, pp. 1393–1395.

GenBank Accession No. U64197.
GenBank Accession No. U83171.
SWISS–PROT Accession No. P48061.

Alkhatib et al., 1996, "CC CKR5: A RANTES, MIP–1α, MIP–1β receptor as a fusion cofactor for macrophage–tropic HIV–1", Science 272:1955–1958.

Baggiolini et al., 1994, "Interleukin–8 and related chemotactic cytokines–CXC and CC chemokines", Adv. in Immunol. 55:97–179.

Barin et al., 1985, "Virus envelope protein of HTLV–III represents major target antigen for antibodies in AIDS patients", Science 228:1094–1096.

Barre–Sinoussi et al., 1983, "Isolation of a T–Lymphotropic retrovirus from a patient at risk for acquired immune deficiency syndrome (AIDS)", Science 220:868–870.

Beall et al., 1992, "Conversion of monocyte chemoattractant protein–1 into a neutrophil attractant by substitution of two amino acids", J. Biol. Chem. 267:3455–3459.

Bischoff et al., 1993, "RANTES and related chemokines activate human basophil granulocytes through different G protein–coupled receptors", Eur. J. Immunol. 23:761–767.

Blazevic et al., 1995, "Helper and cytotoxic T cell responses of HIV type 1–Infected individuals to synthetic peptides of HIV type 1 rev", AIDS Res. & Hum Retroviruses 11:1335–1342.

Charo et al., 1994, "Molecular cloning and functional expression of two monocyte chemoattractant protein 1 receptors reveals alternative splicing of the carboxyl–terminal tails", Proc. Natl. Acad. Sci. USA 91:2752–2756.

Cheng–Mayer et al., 1991, "Host range, replicative, and cytopathic properties of human immunodeficiency virus type 1 are determined by very few amino acid changes in tat an gp120", J. Virol. 65:6931–6941.

Choe et al., 1996, "The β–Chemokine receptors CCR3 and CCR5 facilitate infection by primary HIV–1 isolates", Cell 85:1135–1148.

Clavel et al., 1986, "Isolation of a new human retrovirus from west african patients with AIDS", Science 233:343–346.

(List continued on next page.)

Primary Examiner—Laurie Scheiner
Assistant Examiner—Jeffrey S. Parkin
(74) Attorney, Agent, or Firm—Rothwell, Figg, Ernst & Manbeck, p.c.

(57) ABSTRACT

The present invention relates to therapeutic compositions of macrophage derived chemokine (MDC) and methods for treating and preventing infection by a lentivirus, particularly an immunodeficiency virus, particularly HIV, using MDC proteins, nucleic acids and/or derivatives or analogues thereof. The present invention further relates to methods for detection and prognosis of lenivirus infection, particularly HIV infection using MDC as a prognostic indicator. The present invention further provides MDC proteins, nucleic acids encoding such proteins, that have amino-terminal sequences that differ from other MDC isolates. Recombinant host cells and methods of production are also provided.

16 Claims, 7 Drawing Sheets

OTHER PUBLICATIONS

Figures 1A, 1B:
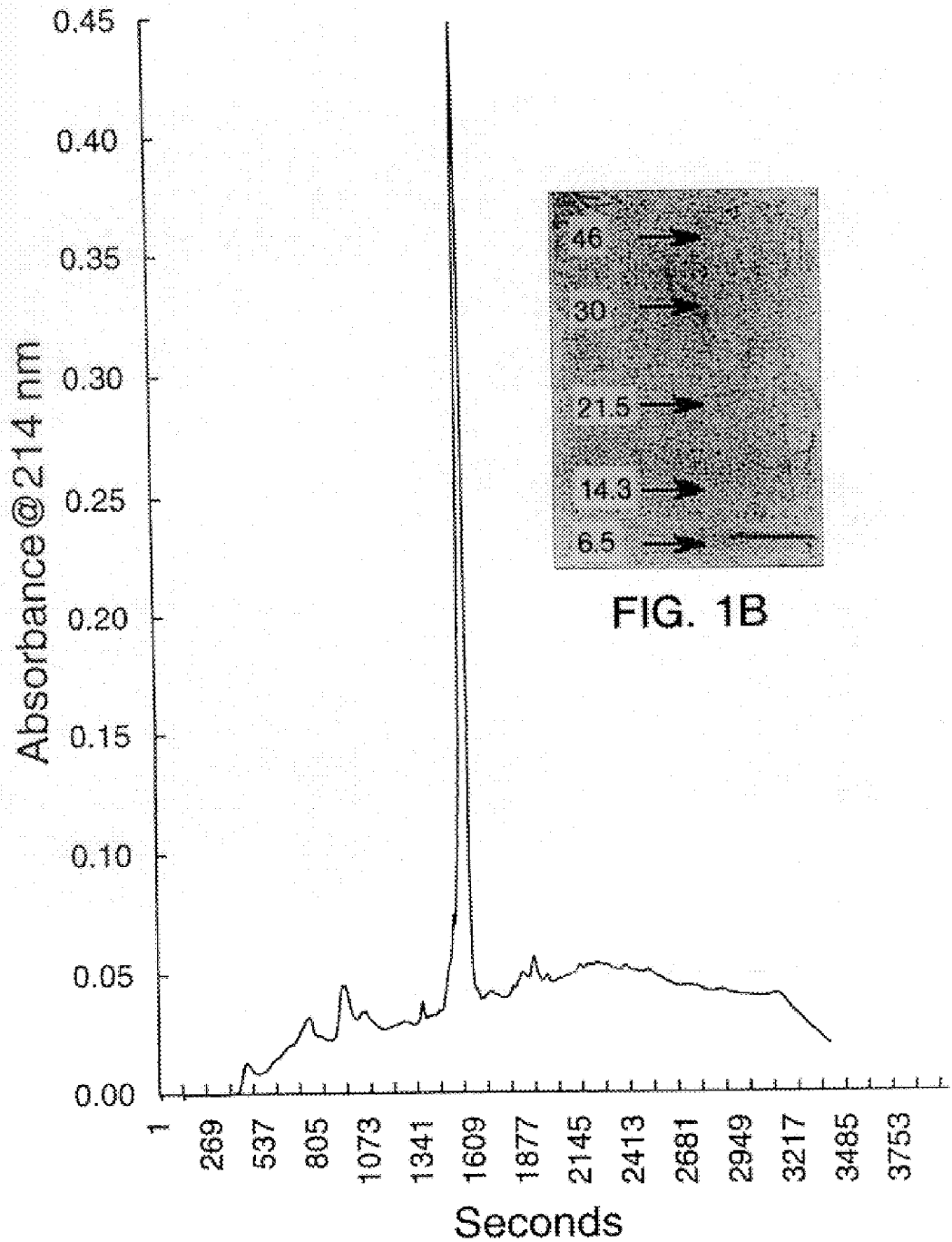

Cocchi et al., 1995, "Identification of RANTES, MIP–1α, and MIP–1β as the major HIV–Suppressive factors produced by CD8+ T cells", *Science* 270:1811–1815.

Cocchi et al., 1996, "The V3 domain of the HIV–1 gp120 envelope glycoprotein is critical for chemokine–mediated blockade of infection", *Nature Med.* 2:1244–1247.

Daar et al., 1990, "HIgh concentrations of recombinant soluble CD4 are required to neutralize primary human immunodeficiency virus type 1 isolates", *Proc. Natl. Acad. Sci. USA* 87:6574–6579.

Dalgleish et al., 1984, "The CD4 (T4) antigen is an essential component of the receptor for the AIDS retrovirus", *Nature* 312:763–767.

Daugherty et al., 1996, "Cloning expression, and characterization of the human eosinophil eotaxin receptor", *J. Exp. Med.* 183:2349–2354.

Deng et al., 1996, "Identification of a major co–receptor for primary isolates of HIV–1", *Nature* 381:661–666.

Doranz et al., 1996, "A dual–tropic primary HIV–1 isolate that uses fusin and the β–chemokine receptors CKR–5, CKR–3, and CKR–2b as fusion cofactors", *Cell* 85:1149–1158.

Dragic et al., 1996,"HIV–1 entry into CD4+ cells is mediated by the chemokine receptor CC–CKR–5", *Nature* 381:667–674.

Erickson et al., 1990, "Design, activity, and 2.8 Å crystal structure of a $C_2$ symmetric inhibitor complexed to HIV–1 protease", *Science* 249:527–533.

Feng et al., 1996, "HIV–1 entry cofactor: Functional cDNA cloning of a seven–transmembrane, G protein–coupled receptor", *Science* 272:872–877.

and isolation of cytopathic retroviruses (HTLV–III) from.

Gardner et al., 1981, "The complete nucleotide sequence of an infectious clone of cauliflower mosaic virus by M13mp7 shotgun sequencing", *Nuc. Acids Res.* 9:2871–2888.

Gerard & Gerard, 1994, "The pro–inflammatory seven-–transmembrane segment receptors of the leukocyte", *Curr. Opin. in Immunol.* 6:140–145.

Godiska et al., 1997, "Human macrophage–derived chemokine (MDC), a novel chemoattractant for monocytes, monocyte–derived dendritic cells, and natural killer cells", J. Exp. Med. 185:1595–1604.

Goff et al., 1981, "Isolation and properties of Maloney murine leukemia virus mutants: Use of a rapid assay for release of virion reverse transcriptase",*J. Virol.* 38:239–248.

Gong et al., 1996, "RANTES and MCP–3 antagonists bind multiple chemokine receptors", *J. Biol. Chem.* 271:10521–10527.

Guyader et al., 1987, "Genome organization and transactivation of the human immunodeficiency virus type 2",*Nature* 326:662–669.

Hammerskjold & Rekosh, 1989, "The molecular biology of the human immunodeficiency virus", *Biochem. Biophys. Acta* 989:269–280.

R. Horuk, 1994, "Molecular properties of the chemokine receptor family", *Trends Pharmacol. Sci.* 15:159–165.

Horuk et al., 1994, "Identification and characterization of a promiscuous chemokine–binding protein in a human erythroleukemic cell line", *J. Biol. Chem.* 269:17730–17733.

Hwang et al., 1991, "Identification of the envelope V3 loop as the primary determinant of cell tropism in HIV–1", *Science* 253:71–74.

Kahn et al., 1990, "The safety and pharmacokinetics of recombinant soluble CD4 (rCD4) in subjects with the acquired immunodeficiency syndrome (AIDS) and AIDS–related complex", *Ann. Int. Med.* 112:254–261.

Kelner et al., 1994, "Lymphotactin: A cytokine that represents a new class of chemokine", *Science* 266:1395–1399.

Kim et al., 1995, "V3–Independent determinants of macrophage tropism in a primary human immunodeficiency virus type 1 isolate", *J. Virol.* 69:1755–1761.

Kitaura et al., 1996, "Molecular cloning of human eotaxin, an eosinophil–selective CC chemokine, and identification of a specific eosinophil eotaxin receptor, cc chemokine receptor 3", *J. Biol. Chem.* 271:7725–7730.

Klatzmann et al., 1984, "T–lymphocyte T4 molecule behaves as the receptor for human retrovirus LAV", *Nature* 312:767–768.

Klotman et al., 1997, "HIV–1 inhibitory activity of CD8+ cell supernatants is distinct from that of RANTES, MIP–1α and MIP–1β", Conference on Advances in AIDS Vaccine Development: 9th Annual Meeting of National Cooperative Vaccine Development Group, May 1997.

Kunz et al., 1991, "The human leukocyte platelet–activating factor receptor—cDNA cloning, cell surface expression, and construction of a novel epitope–bearing analog", *J. Biol. Chem.* 267:9101–9106.

J.M.A. Lange, 1995, "Triple combinations: Present and future", *J. AIDS Synd. & Hum. Retrovirol.* 10:S77–82.

Liu et al., 1996, "Homozygous defect in HIV–1 coreceptor accounts for resistance of some multiply–exposed individuals to HIV–1 infection", *Cell* 86:367–377.

Loestcher et al., 1996, "Chemokine receptor specific for IP10 and mig: Structure, function, and expression in activated T–lymphocytes", *J. Exp. Med.* 184:963–969.

Maddon et al., 1986, "The T4 gene encodes the AIDS virus receptor and is expressed in the immune system and the brain", *Cell* 47:333–348.

McDougal et al., 1986, "Binding of HTLV–III/LAV to T4+ T cells by a complex of the 110K viral protein and the T4 molecule", *Science* 231:382–385.

Miedema et al., 1994, "Changing virus–host interactions in the course of HIV–1 infection", *Immunol. Rev.* 140:35–72.

Miller & Krangel, 1992, "Biology and biochemistry of the chemokines: A family of chemotactic and inflammatory cytokines", *Crit. Rev. in Immunol.* 12:17–46.

Mitsuya et al., 1991, "Targeted therapy of human immunodeficiency virus–related disease", *FASEB J.* 5:2369–2381.

Mitsuya et al., 1990, "Molecular targets for AIDS therapy", *Science* 249:1533–1544.

P.M. Murphy, 1994, "The molecular biology of leukocyte chemoattractant receptors", *Annu. Rev. Immunol.* 12:593–633.

Neote et al., 1993, "Identification of a promiscuous inflammatory peptide receptor on the surface of red blood cells", *J. Biol. Chem.* 268:12247–12249.

Neote et al., 1993, "Molecular cloning, functional expression, and signaling characteristics of a C–C chemokine receptor", *Cell* 72:415–425.

Neote et al., 1994, "Functional and biochemical analysis of the cloned duffy antigen: Identity with the red blood cell chemokine receptor", *Blood* 84:44–52.

O'Brien et al., 1990, "HIV–1 tropism for mononuclear phagocytes can be determined by regions of gp120 outside the CD4–binding domain", *Nature* 348:69–73.

Oravecz et al., 1996, "β–chemokine inhibition of monocytotropic HIV–1 infection", *J. Immunol.* 157:1329–1332.

Pal et al., 1993, "Conformational perturbation of the envelope glycoprotein gp120 of human immunodeficiency virus type 1 by soluble CD4 and the lectin succinyl Con A", *Virol.* 194:833–837.

Paxton et al., 1996, "Relative resistance to HIV–1 infection of CD4 lymphocytes from persons who remain uninfected despite multiple high–risk sexual exposures", *Nature Med.* 2:412–417.

Perelson et al., 1996, "HIV–1 dynamics in vivo: Virion clearance rate, infected cell life–span, and viral generation time", *Science* 15:1582–1586.

Ponath et al., 1996, "Cloning of the human eosinophil chemoattractant, eotaxin", *J. Clin. Invest.* 97:604–612.

Ponath et al., 1996, "Molecular cloning and characterization of a human eotaxin receptor expressed selectively on eosinophils", *J. Exp. Med.* 183:2437–2438.

Power et al., 1995, "Molecular cloning and functional expression of a novel cc chemokine receptor cDNA from a human basophilic cell line", *J. Biol. Chem.* 270:19495–19500.

Proudfoot et al., 1996, "Extension of recombinant human RANTES by the retention of the initiating methionine produces a potent antagonist", *J. Biol. Chem.* 271:2599–2603.

Raport et al., 1996, "Molecular cloning and functional characterization of a novel human CC chemokine receptor (CCR5) for RANTES, MIP–1β, and MIP–1α", J. Biol. Chem. 271:17161–17166.

Raport et al., 1996, "New members of the chemokine receptor gene family", J. Leukoc. Biol. 59:18–23.

Rossi et al., 1997, "Identification through bioinformatics of two new macrophage proinflammatory human chemokines", *J. Immunol.* 158:1033–1036.

Samson et al., 1996, "Molecular cloning and functional expression of a new human cc–chemokine receptor gene", *Biochem.* 35:3362–3367.

Sattentau & Moore, 1993, "The role of CD4 in HIV binding and entry", *Philos. Trans. R. Soc. London* (*Biol.*) 342:59–66.

T.J. Schall, 1991, "Biology of the RANTES/SIS cytokine family", *Cytokine* 3:165–183.

Schooley et al., 1990, "Recombinant soluble CD4 therapy in patients with the acquired immunodeficiency syndrome (AIDS) and AIDS–related complex", *Ann. Int. Med.* 112:247–253.

Simon et al., 1991, "Diversity of G proteins in signal transduction", *Science* 252:802–807.

Smith et al., 1987, "Blocking of HIV–1 infectivity by a soluble, secreted form of the CD4 antigen", *Science* 238:1704–1707.

Teich et al., 1984, *RNA Tumor Viruses* Weiss et al. (eds.), CSH–Press, pp. 949–956.

H. Varmus, 1988, "Retroviruses", *Science* 240:1427–1439.

Weiss et al., 1996, "HIV receptors and the pathogenesis of AIDS", *Science* 272:1885–1886.

Willey et al., 1988, "In vitro mutagenesis identifies a region within the envelope gene of the human immunodeficiency virus that is critical for infectivity", *J. Virol.* 62:139–147.

Yarchoan et al., 1989, "Phase 1 study of the administration of recombinant soluble CD4 (rCD4) by continuous infusion to patients with AIDS or ARC", *Proc. 5th Int. Conf. on AIDS* MCP 137, p. 564.

Yoshida et al., 1995, "Molecular cloning of a novel C or γ type chemokine, SCM–1", *FEBS Lett.* 360:155–159.

Zhang et al., 1996, "HIV–1 subtype and second–receptor use", *Nature* 383:768.

* cited by examiner

```
GAGACATACA GGACAGAGC ATG GCT CGC CTA CAG ACT GCA CTC CTG GTT GTC        52
                    Met Ala Arg Leu Gln Thr Ala Leu Leu Val Val
                    -24         -20                     -15
CTC GTC CTC CTT GCT GTG GCG CTT CAA GCA ACT GAG GCA GGC CCC TAC        100
Leu Val Leu Leu Ala Val Ala Leu Gln Ala Thr Glu Ala Gly Pro Tyr
            -10             -5                          1
GGC GCC AAC ATG GAA GAC AGC GTC TGC TGC CGT GAT TAC GTC CGT TAC        148
Gly Ala Asn Met Glu Asp Ser Val Cys Cys Arg Asp Tyr Val Arg Tyr
        5                   10                  15
CGT CTG CCC CTG CGC GTG GTG AAA CAC TTC TAC TGG ACC TCA GAC TCC        196
Arg Leu Pro Leu Arg Val Val Lys His Phe Tyr Trp Thr Ser Asp Ser
20                  25                  30                  35
TGC CCG AGG CCT GGC GTG GTG TTG CTA ACC TTC AGG GAT AAG GAG ATC        244
Cys Pro Arg Pro Gly Val Val Leu Leu Thr Phe Arg Asp Lys Glu Ile
                40                  45                  50
TGT GCC GAT CCC AGA GTG CCC TGG GTG AAG ATG ATT CTC AAT AAG CTG        292
Cys Ala Asp Pro Arg Val Pro Trp Val Lys Met Ile Leu Asn Lys Leu
            55                  60                  65
AGC CAA TGAAGAGCCT ACTCTGATGA CCGTGGCCTT GGCTCCTCCA GGAAGGCTCA        348
Ser Gln
GGAGCCCTAC CTCCCTGCCA TTATAGCTGC TCCCCGCCAG AAGCCTGTGC CAACTCTCTG      408
CATTCCCTGA TCTCCATCCC TGTGGCTGTC ACCCTTGGTC ACCTCCGTGC TGTCACTGCC      468
ATCTCCCCCC TGACCCCTCT AACCCATCCT CTGCCTCCCT CCCTGCAGTC AGAGGGTCCT      528
GTTCCCATCA GCGATTCCCC TGCTTAAACC CTTCCATGAC TCCCCACTGC CCTAAGCTGA      588
GGTCAGTCTC CCAAGCCTGG CATGTGGCCC TCTGGATCTG GGTTCCATCT CTGTCTCCAG      648
CCTGCCCACT TCCCTTCATG AATGTTGGGT TCTAGCTCCC TGTTCTCCAA ACCCATACTA      708
CACATCCCAC TTCTGGGTCT TGCCTGGGA GTTGCTGAC ACTCAGAAAG TCCCACCACC        768
TGCACATGTG TAGCCCCACC AGCCCTCCAA GGCATTGCTC GCCCAAGCAG CTGGTAATTC      828
CATTTCATGT ATTAGATGTC CCCTGGCCCT CTGTCCCCTC TTAATAACCC TAGTCACAGT      888
CTCCGCAGAT TCTTGGGATT TGGGGGTTTT CTCCCCCACC TCTCCACTAG TTGGACCAAG      948
GTTTCTAGCT AAGTTACTCT AGTCTCCAAG CCTCTAGCAT AGAGCACTGC AGACAGGCCC     1008
TGGCTCAGAA TCAGAGCCCA GAAAGTGGCT GCAGACAAAA TCAATAAAAC TAATGTCCCT     1068
CCCCTCTCCC TGCCAAAAGG CAGTTACATA TCAATACAGA GACTCAAGGT CACTAGAAAT     1128
GGGCCAGCTG GGTCAATGTG AAGCCCCAAA TTTGCCCAGA TTCACCTTTC TTCCCCCACT     1188
CCCTTTTTTT TTTTTTTTTT TTTGAGATGG AGTTTCGCTC TTGTCACCCA CGCTGGAGTG     1248
CAATGGTGTG GTCTTGGCTT ATTGAAGCCT CTGCCTCCTG GGTTCAAGTG ATTCTCTTGC     1308
CTCAGCCTCC TGAGTAGCTG GGATTACAGG TTCCTGCTAC CACGCCCAGC TAATTTTTGT     1368
ATTTTTAGTA GAGACGAGGC TTCACCATGT TGGCCAGGCT GGTCTCGAAC TCCTGTCCTC     1428
AGGTAATCCG CCCACCTCAG CCTCCCAAAG TGCTGGGATT ACAGGCGTGA GCCACAGTGC     1488
CTGGCCTCTT CCCTCTCCCC ACTGCCCCCC CCAACTTTTT TTTTTTTTTT ATGGCAGGGT     1548
```

FIG. 5A-1

```
CTCACTCTGT CGCCCAGGCT GGAGTGCAGT GGCGTGATCT CGGCTCACTA CAACCTCGAC  1608
CTCCTGGGTT CAAGTGATTC TCCCACCCCA GCCTCCCAAG TAGCTGGGAT ACAGGTGTG   1668
TGCCACTACG GCTGGCTAAT TTTTGTATTT TTAGTAGAGA CAGGTTTCAC CATATTGGCC  1728
AGGCTGGTCT TGAACTCCTG ACCTCAAGTG ATCCACCTTC CTTGTGCTCC CAAAGTGCTG  1788
AGATTACAGG CGTGAGCTAT CACACCCAGC CTCCCCCTTT TTTTCCTAAT AGGAGACTCC  1848
TGTACCTTTC TTCGTTTTAC CTATGTGTCG TGTCTGCTTA CATTTCCTTC TCCCCTCAGG  1908
CTTTTTTTGG GTGGTCCTCC AACCTCCAAT ACCCAGGCCT GGCCTCTTCA GAGTACCCCC  1968
CATTCCACTT TCCCTGCCTC CTTCCTTAAA TAGCTGACAA TCAAATTCAT GCTATGGTGT  2028
GAAAGACTAC CTTTGACTTG GTATTATAAG CTGGAGTTAT ATATGTATTT GAAAACAGAG  2088
TAAATACTTA AGAGGCCAAA TAGATGAATG AAGAATTTT AGGAACTGTG AGAGGGGGAC   2148
AAGGTGAAGC TTTCCTGGCC CTGGGAGGAA GCTGGCTGTG GTAGCGTAGC GCTCTCTCTC  2208
TCTGTCTGTG GCAGGAGCCA AAGAGTAGGG TGTAATTGAG TGAAGGAATC CTGGGTAGAG  2268
ACCATTCTCA GGTGGTTGGG CCAGGCTAAA GACTGGGAGT TGGGTCTATC TATGCCTTTC  2328
TGGCTGATTT TTGTAGAGAC GGGGTTTTGC CATGTTACCC AGGCTGGTCT CAAACTCCTG  2388
GGCTCAAGCG ATCCTCCTGG CTCAGCCTCC CAAAGTGCTG GGATTACAGG CGTGAATCAC  2448
TGCGCCTGGC TTCCTCTTCC TCTTGAGAAA TATTCTTTTC ATACAGCAAG TATGGGACAG  2508
CAGTGTCCCA GGTAAAGGAC ATAAATGTTA CAAGTGTCTG GTCCTTTCTG AGGGAGGCTG  2568
GTGCCGCTCT GCAGGGTATT TGAACCTGTG GAATTGGAGG AGGCCATTTC ACTCCCTGAA  2628
CCCAGCCTGA CAAATCACAG TGAGAATGTT CACCTTATAG GCTTGCTGTG GGGCTCAGGT  2688
TGAAAGTGTG GGGAGTGACA CTGCCTAGGC ATCCAGCTCA GTGTCATCCA GGGCCTGTGT  2748
CCCTCCCGAA CCCAGGGTCA ACCTGCCTGC CACAGGCACT AGAAGGACGA ATCTGCCTAC  2808
TGCCCATGAA CGGGGCCCTC AAGCGTCCTG GGATCTCCTT CTCCCTCCTG TCCTGTCCTT  2868
GCCCCTCAGG ACTGCTGGAA AATAAATCCT TTAAAATAGT AAAAAAAAAA AAAA        2923
```

FIG. 5A-2

```
Met Ala Arg Leu Gln Thr Ala Leu Leu Val Val Leu Val Leu Leu Ala
-24           -20                 -15                 -10
Val Ala Leu Gln Ala Thr Glu Ala Gly Pro Tyr Gly Ala Asn Met Glu
            -5                1                   5
Asp Ser Val Cys Cys Arg Asp Tyr Val Arg Tyr Arg Leu Pro Leu Arg
        10              15              20
Val Val Lys His Phe Tyr Trp Thr Ser Asp Ser Cys Pro Arg Pro Gly
25              30              35                          40
Val Val Leu Leu Thr Phe Arg Asp Lys Glu Ile Cys Ala Asp Pro Arg
                45              50                          55
Val Pro Trp Val Lys Met Ile Leu Asn Lys Leu Ser Gln
            60              65
```

FIG. 5B

SEQUENCE LISTING

```
<160> NUMBER OF SEQ ID NOS: 4

<210> SEQ ID NO 1
<211> LENGTH: 2923
<212> TYPE: DNA
<213> ORGANISM: Homo sapiens
<220> FEATURE:
<221> NAME/KEY: mat_peptide
```

<222> LOCATION: (92)..(298)
<220> FEATURE:
<221> NAME/KEY: CDS
<222> LOCATION: (20)..(298)

<400> SEQUENCE: 1

```
gagacataca ggacagagc atg gct cgc cta cag act gca ctc ctg gtt gtc         52
                    Met Ala Arg Leu Gln Thr Ala Leu Leu Val Val
                                 -20                 -15 ctc gtc ctc ctt gct gtg gcg ctt caa gca act gag gca ggc ccc tac         100
Leu Val Leu Leu Ala Val Ala Leu Gln Ala Thr Glu Ala Gly Pro Tyr
            -10                 -5                 -1   1 ggc gcc aac atg gaa gac agc gtc tgc tgc cgt gat tac gtc cgt tac         148
Gly Ala Asn Met Glu Asp Ser Val Cys Cys Arg Asp Tyr Val Arg Tyr
         5                  10                  15 cgt ctg ccc ctg cgc gtg gtg aaa cac ttc tac tgg acc tca gac tcc         196
Arg Leu Pro Leu Arg Val Val Lys His Phe Tyr Trp Thr Ser Asp Ser
 20                  25                  30                  35 tgc ccg agg cct ggc gtg gtg ttg cta acc ttc agg gat aag gag atc         244
Cys Pro Arg Pro Gly Val Val Leu Leu Thr Phe Arg Asp Lys Glu Ile
                 40                  45                  50 tgt gcc gat ccc aga gtg ccc tgg gtg aag atg att ctc aat aag ctg         292
Cys Ala Asp Pro Arg Val Pro Trp Val Lys Met Ile Leu Asn Lys Leu
             55                  60                  65 agc caa tgaagagcct actctgatga ccgtggcctt ggctcctcca ggaaggctca         348
Ser Gln ggagccctac ctccctgcca ttatagctgc tccccgccag aagcctgtgc caactctctg        408
cattccctga tctccatccc tgtggctgtc acccttggtc acctccgtgc tgtcactgcc        468
atctccccc  tgacccctct aacccatcct ctgcctccct cctgcagtc  agagggtcct       528
gttcccatca gcgattcccc tgcttaaacc cttccatgac tccccactgc cctaagctga        588
ggtcagtctc ccaagcctgg catgtggccc tctggatctg ggttccatct ctgtctccag        648
cctgccact  tcccttcatg aatgttgggt tctagctccc tgttctccaa acccatacta        708
cacatcccac ttctgggtct ttgcctggga tgttgctgac actcagaaag tcccaccacc        768
tgcacatgtg tagccccacc agccctccaa ggcattgctc cccaagcag  ctggtaattc        828
catttcatgt attagatgtc ccctggccct ctgtcccctc ttaataaccc tagtcacagt        888
ctccgcagat tcttgggatt tggggttttt ctcccccacc tctccactag ttggaccaag        948
gtttctagct aagttactct agtctccaag cctctagcat agagcactgc agacaggccc       1008
tggctcagaa tcagagccca gaaagtggct gcagacaaaa tcaataaaac taatgtccct       1068
cccctctccc tgccaaaagg cagttacata tcaatacaga gactcaaggt cactagaaat       1128
gggccagctg ggtcaatgtg aagccccaaa tttgcccaga ttcacctttc ttccccact       1188
cccttttttt ttttttttt  tttgagatgg agtttcgctc ttgtcaccca cgctggagtg       1248
caatggtgtg gtcttggctt attgaagcct ctgcctcctg ggttcaagtg attctcttgc       1308
ctcagcctcc tgagtagctg ggattacagg ttcctgctac cacgcccagc taatttttgt       1368
atttttagta gagacgaggc ttcaccatgt tggccaggct ggtctcgaac tcctgtcctc       1428
aggtaatccg cccacctcag cctcccaaag tgctgggatt acaggcgtga gccacagtgc       1488
ctggcctctt ccctctcccc actgcccccc ccaacttttt tttttttttt atggcagggt       1548
ctcactctgt cgcccaggct ggagtgcagt ggcgtgatct cggctcacta caacctcgac       1608
ctcctgggtt caagtgattc tcccacccca gcctcccaag tagctgggat tacaggtgtg       1668
tgccactacg gctggctaat ttttgtattt ttagtagaga caggtttcac catattggcc       1728
```

```
aggctggtct tgaactcctg acctcaagtg atccaccttc cttgtgctcc caaagtgctg    1788
agattacagg cgtgagctat cacacccagc ctcccccttt ttttcctaat aggagactcc    1848
tgtacctttc ttcgttttac ctatgtgtcg tgtctgctta catttccttc tcccctcagg    1908 cttttttttgg gtggtcctcc aacctccaat acccaggcct ggcctcttca gagtacccccc   1968 cattccactt tccctgcctc cttccttaaa tagctgacaa tcaaattcat gctatggtgt    2028
gaaagactac ctttgacttg gtattataag ctggagttat atatgtattt gaaacagag     2088 taaatactta agaggccaaa tagatgaatg gaagaatttt aggaactgtg agaggggggac   2148 aaggtgaagc tttcctggcc ctgggaggaa gctggctgtg gtagcgtagc gctctctctc    2208
tctgtctgtg gcaggagcca aagagtaggg tgtaattgag tgaaggaatc ctgggtagag    2268
accattctca ggtggttggg ccaggctaaa gactgggagt tgggtctatc tatgcctttc    2328
tggctgattt ttgtagagac ggggttttgc catgttaccc aggctggtct caaactcctg    2388
ggctcaagcg atcctcctgg ctcagcctcc caaagtgctg ggattacagg cgtgaatcac    2448
tgcgcctggc ttcctcttcc tcttgagaaa tattcttttc atacagcaag tatgggacag    2508
cagtgtccca ggtaaaggac ataaatgtta caagtgtctg gtcctttctg agggaggctg    2568
gtgccgctct gcagggtatt tgaacctgtg gaattggagg aggccatttc actccctgaa    2628
cccagcctga caaatcacag tgagaatgtt caccttatag gcttgctgtg gggctcaggt    2688
tgaaagtgtg gggagtgaca ctgcctaggc atccagctca gtgtcatcca gggcctgtgt    2748
ccctcccgaa cccagggtca acctgcctgc cacaggcact agaaggacga atctgcctac    2808
tgcccatgaa cggggccctc aagcgtcctg ggatctcctt ctccctcctg tcctgtcctt    2868
gcccctcagg actgctggaa aataaatcct ttaaaatagt aaaaaaaaaa aaaaa         2923

<210> SEQ ID NO 2
<211> LENGTH: 93
<212> TYPE: PRT
<213> ORGANISM: Homo sapiens

<400> SEQUENCE: 2

Met Ala Arg Leu Gln Thr Ala Leu Leu Val Val Leu Val Leu Ala
                -20             -15                 -10

Val Ala Leu Gln Ala Thr Glu Ala Gly Pro Tyr Gly Ala Asn Met Glu
            -5              -1   1               5

Asp Ser Val Cys Cys Arg Asp Tyr Val Arg Tyr Arg Leu Pro Leu Arg
     10              15              20

Val Val Lys His Phe Tyr Trp Thr Ser Asp Ser Cys Pro Arg Pro Gly
 25              30              35                      40

Val Val Leu Leu Thr Phe Arg Asp Lys Glu Ile Cys Ala Asp Pro Arg
                45              50              55

Val Pro Trp Val Lys Met Ile Leu Asn Lys Leu Ser Gln
            60              65

<210> SEQ ID NO 3
<211> LENGTH: 19
<212> TYPE: PRT
<213> ORGANISM: Homo sapiens
<220> FEATURE:
<221> NAME/KEY: SITE
<222> LOCATION: (10)..(11)
<223> OTHER INFORMATION: Xaa is an unknown amino acid

<400> SEQUENCE: 3
```

```
Tyr Gly Ala Asn Met Glu Asp Ser Val Xaa Xaa Arg Asp Tyr Val Arg
 1               5                  10                  15

Tyr Arg Leu

<210> SEQ ID NO 4
<211> LENGTH: 13
<212> TYPE: PRT
<213> ORGANISM: Homo sapiens
<220> FEATURE:
<221> NAME/KEY: SITE
<222> LOCATION: (11)..(12)
<223> OTHER INFORMATION: Xaa is an unknown amino acid

<400> SEQUENCE: 4

Pro Tyr Gly Ala Asn Met Glu Asp Ser Val Xaa Xaa Arg
 1               5                  10
```

MACROPHAGE DERIVED CHEMOKINE (MDC) AS AN ANTI-VIRAL AGENT FOR THE TREATMENT AND PREVENTION OF LENTIVIRUS INFECTION

The invention was made with Government support under Contract No. N01-AI-55279 awarded by the National Institutes of Health. The Government has certain rights in the invention.

1. INTRODUCTION

The present invention relates to therapeutic compositions of macrophage derived chemokine (MDC) and methods for treating and preventing infection by a lentivirus, in particular an immunodeficiency virus, particularly HIV infection, using MDC proteins, nucleic acids and/or derivatives or analogues thereof. The present invention further relates to methods of prognosis for a lentivirus infection, particularly an HIV infection using the MDC as a prognostic indicator.

2. BACKGROUND OF THE INVENTION

Human immunodeficiency virus (HIV) induces a persistent and progressive infection leading, in the vast majority of cases, to the development of the acquired immunodeficiency syndrome (AIDS) (Barre-Sinoussi et al., 1983, *Science* 220:868–870; Gallo et al., 1984, *Science* 224:500–503). There are at least two distinct types of HIV: HIV-1 (Barre-Sinoussi et al., 1983, *Science* 220:868–870; Gallo et al., 1984, *Science* 224:500–503) and HIV-2 (Clavel et al., 1986, *Science* 233:343–346; Guyader et al., 1987, *Nature* 326:662–669). In humans, HIV replication occurs prominently in $CD4^+$ T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses (Teich et al., 1984, RNA Tumor Viruses, Weiss et al., eds., CSH-press, pp. 949–956). Retroviruses are small enveloped viruses that contain a single-stranded RNA genome, and replicate via a DNA intermediate produced by a virally-encoded reverse transcriptase, an RNA-dependent DNA polymerase (Varmus, H., 1988, *Science* 240:1427–1439). Other retroviruses include, for example, oncogenic viruses such as human T-cell leukemia viruses (HTLV-1, -II,-III), and feline leukemia virus.

Lentiviruses are a subfamily of the retroviruses which include the classic ungulate lentiviruses (visna virus of sheep, caprine arthritis encephalitis virus and equine infectious anemia virus) and the immunodeficiency viruses of humans (HIV), monkeys (SIV), cats (FIV) and cattle (BIV).

Lentivirus particles are approximately 80–110 nm in size and consist of an RNA genome and viral enzymes enclosed in a core of viral proteins encased by a cell-derived membrane spiked with viral envelope glycoproteins. Lentiviruses can be distinguished from other subgroups of retroviruses by a cylindrical or rod-shaped nucleoid in mature particles and the absence of preformed particles in the cytoplasm. Lentiviruses are not oncogenic, but produce long-term, persistent infections which eventually lead to chronic debilitating disease. All lentiviruses studied to date replicate and persist in cells of the monocyte/macrophage lineage. See *Encyclopedia of Virology*, Vol. 3, page 1316 (Academic Press Limited, London, England, 1994).

The HIV viral particle consists of a viral core, composed in part of capsid proteins designated p24 and p17, together with the viral RNA genome and those enzymes required for replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kilodalton precursor protein which is cleaved by a cellular protease during viral budding into two glycoproteins, gp41 and gp120. gp41 is a transmembrane glycoprotein and gp120 is an extracellular glycoprotein which remains non-covalently associated with gp41, possibly in a trimeric or multimeric form (Hammerskjold, M. and Rekosh, D., 1989, *Biochem. Biophys. Acta* 989:269–280).

HIV, like other enveloped viruses, introduces viral genetic material into the host cell through a viral-envelope mediated fusion of viral and target membranes. HIV is targeted to $CD4^+$ cells because a CD4 cell surface protein (CD4) acts as the cellular receptor for the HIV-1 virus (Dalgleish et al., 1984, *Nature* 312:763–767; Klatzmann et al., 1984, *Nature* 312:767–768; Maddon et al., 1986, *Cell* 47:333–348). Viral entry into cells is dependent upon gp120 binding the cellular CD4 receptor molecules (Pal et al., 1993, *Virology* 194:833–837; McDougal et al., 1986, *Science* 231:382–385; Maddon et al., 1986, *Cell* 47:333–348), explaining HIV's tropism for $CD4^+$ cells, while gp41 anchors the envelope glycoprotein complex in the viral membrane. The binding of gp120 to CD4 induces conformational changes in the viral glycoproteins, but this binding alone is insufficient to lead to infection (reviewed by Sattentau and Moore, 1993, *Philos. Trans. R. Soc. London* (Biol.) 342:59–66).

Studies of HIV-1 isolates have revealed a heterogeneity in their ability to infect different human cell types (reviewed by Miedema et al., 1994, *Immunol. Rev.* 140:35–72). The majority of extensively passaged laboratory strains of HIV-1 readily infect cultured T cell lines and primary T lymphocytes, but not primary monocytes or macrophages. These strains are termed T-tropic. T-tropic HIV-1 strains are more likely to be found in HIV-1 infected individuals during the late stages of infection (Weiss et al., 1996, *Science* 272:1885–1886). The majority of primary HIV-1 isolates (i.e., viruses not extensively passaged in culture) replicate efficiently in primary lymphocytes, monocytes and macrophages, but grow poorly in established T cell lines. These isolates have been termed M-tropic. The viral determinant of T- and M- tropism maps to alterations in the third variable region of gp120 (the V3 loop) (Choe et al., 1996, *Cell* 85:1135–1148; Cheng-Mayer et al., 1991, *J. Virol.* 65:6931–6941; Hwang et al., 1991, *Science* 253:71–74; Kim et al., 1995, *J. Virol.* 69:1755–1761; and O'Brien et al., 1990, *Nature* 348:69–73). The characterization of HIV isolates with distinct tropisms taken together with the observation that binding to the CD4 cell surface protein alone is insufficient to lead to infection, suggest that cell-type specific cofactors might be required in addition to CD4 for HIV-1 entry into the host cell.

The chemokine receptor CCR5 is normally present in cells of the host and serves as the natural receptor for the β cysteine-cysteine chemokines RANTES, MIP-1α, and MIP-1β. It serves in addition, however, as a co-receptor for HIV-1 (Feng et al., *Science* 272:872–877; Cocchi et al., *Science* 270:1811–1815.)

CCR5 is a seven transmembrane domain, G-protein-coupled protein that is expressed on the surfaces of CD4+ and CD8+ T lymphocytes (types of human peripheral blood mononuclear cells (PBMC) (Raport et al. 1996, *J. Biol. Chem.* 271:17161–17166), and on KG-1A promyeloblastic cells (Samson et al., 1996, *Biochemistry* 35:3362–3367). The binding of β cysteine-cysteine chemokines to CCR5 to these cells triggers a variety of normal cellular events in leukocytes (white blood cells) including increases in intracellular calcium, tyrosine kinase activity and chemotaxis towards areas of inflammation.

In addition to serving these normal signal-transduction and immune response functions, CCR5 serves as a co-receptor that facilitates the attachment and fusion of certain primary M-tropic, non-syncytium inducing strains of HIV-1, to their target cells, i.e., monocyte-macrophages and primary CD4+ T lymphocytes.

Because the chemokines RANTES, MIP-1α and MIP-1β compete with HIV-1 for binding to CCR5, they act as natural suppressors of HIV-1 infection (Cocchi et al., 1995, *Science* 270:1811–1815; Baier et al. 1995, *Nature* 378:563) and may be part of the body's general defenses against many types of viruses. Cocchi et al. (1995, *Science* 270:1811–1815) have shown that RANTES, MIP-1α and MIP-1β inhibit infection of monocyte-macrophages and CD4+ T cells by M-tropic HIV-1. They inhibit HIV infection or replication at a stage prior to HIV transcription.

Recently, certain factors produced by activated CD8+ T cells have been implicated in suppression of HIV infection (Walker et al., 1986, *Science* 234:1563; Brinchman et al., 1990, *J. Immunol.* 144:2961). The production of a suppressive activity correlates with immune status and shows a steady decline in parallel with HIV disease progression (Walker et al., *Cell Immunol.* 119:470; Mackewicz et al., *J. clin. Invest.* 87:1462; Blackbourn et al., 1996, *Proc. Natl. Acad. Sci. USA* 93:13125). The chemokines RANTES (regulated on activation normal T cell expressed and secreted), macrophage-inflammatory protein-1α and -1β (MIP-1α and MIP-1β, respectively), which are secreted by CD8+ T cells, were shown to suppress HIV-1 p24 antigen production in cells infected with HIV-1, HIV-2 or SIV isolates in vitro (Cocchi et al., 1995, *Science* 270:1811–1815). Additionally, high levels of these chemokines have been found to be secreted by CD4+ T lymphocytes in individuals that have been exposed to HIV-1 on multiple occasions, but remain uninfected (Paxton et al., 1996, *Nature Med.* 2:412–417).

However, experiments using acute and endogenous infectivity assays with either primary T cells (Cocchi et al., 1996, *Science* 270:1811; Barker et al., 1996, *J. Immunol.* 156:4476; Paliard et al., 1996, *AIDS* 10:1317; Kinter et al., 1996, *Proc. Natl. Acad. Sci. USA* 93:14076; Rubbert et al., 1997, *AIDS* 13:63) or macrophages (Moriuchi et al., 1996, *Proc. Natl. Acad. Sci. USA* 93:15431) as target cells suggest that the full complement of suppressive activity produced by primary CD8+ T cells is not entirely explained by these chemokines. While RANTES, MIP-1α and MIP-1β alone or in combination, potently suppress a variety of primary HIV-1 isolates and macrophage tropic isolates, such as HIV-$1_{BaL}$, some established laboratory strains, such as HIV-$1_{IIIB}$, are refractory to inhibition of infection or replication by these chemokines (Cocchi et al., 1995, *Science* 270:1811–1815). Levels of RANTES, MIP-1α and MIP-1β do not correlate with the suppression of certain T-tropic, syncytium-inducing (SI) and T cell line adapted (TCLA) isolates and the addition of neutralizing anti-chemokine antibodies does not reverse the suppressive effect (Barker et al., 1996, *J. Immunol.* 156:4476; Paliard et al., 1996, *AIDS* 10:1317; Kinter et al., 1996, *Proc. Natl. Acad. Sci. USA* 93:14076; Rubbert et al., 1997, *AIDS* 13:63). Therefore, additional, unidentified chemokines capable of suppressing HIV-1 are produced by activated T cells.

Chemokines, or chemoattractant cytokines, are a subgroup of immune factors that have been shown to mediate chemotactic and other pro-inflammatory phenomena (See, Schall, 1991, *Cytokine* 3:165–183). Chemokines are small molecules of approximately 70–80 residues in length and can generally be divided into two subgroups, α which have two N-terminal cysteines separated by a single amino acid (CxC) and β which have two adjacent cysteines at the N terminus (CC). RANTES, MIP-1α and MIP-1β are members of the β subgroup (reviewed by Horuk, R., 1994, *Trends Pharmacol. Sci.* 15:159–165; Murphy, P. M., 1994, *Annu. Rev. Immunol.* 12:593–633). The amino terminus of the β chemokines RANTES, MCP-1, and MCP-3 have been implicated in the mediation of cell migration and inflammation induced by these chemokines. This involvement is suggested by the observation that the deletion of the amino terminal 8 residues of MCP-1, amino terminal 9 residues of MCP-3, and amino terminal 8 residues of RANTES and the addition of a methionine to the amino terminus of RANTES, antagonize the chemotaxis, calcium mobilization and/or enzyme release stimulated by their native counterparts (Gong et al., 1996, *J. Biol. Chem.* 271:10521–10527; Proudfoot et al., 1996 *J. Biol. Chem.* 271:2599–2603). Additionally, α chemokine-like chemotactic activity has been introduced into MCP-1 via a double mutation of Tyr 28 and Arg 30 to leucine and valine, respectively, indicating that internal regions of this protein also play a role in regulating chemotactic activity (Beall et al., 1992, *J. Biol. Chem.* 267:3455–3459).

The monomeric forms of all chemokines characterized thus far share significant structural homology, although the quaternary structures of α and β groups are distinct. While the monomeric structures of the β and α chemokines are very similar, the dimeric structures of the two groups are completely different. An additional chemokine, lymphotactin, which has only one N terminal cysteine has also been identified and may represent an additional subgroup (γ) of chemokines (Yoshida et al., 1995, *FEBS Lett.* 360:155–159; and Kelner et al., 1994, *Science* 266:1395–1399).

Receptors for chemokines belong to the large family of G-protein coupled, 7 transmembrane domain receptors (GCR's) (See, reviews by Horuk, R., 1994, *Trends Pharmacol. Sci.* 15:159–165; and Murphy, P. M., 1994, *Annu. Rev. Immunol.* 12:593–633). Competition binding and cross-desensitization studies have shown that chemokine receptors exhibit considerable promiscuity in ligand binding. Examples demonstrating the promiscuity among β chemokine receptors include: CCR-1, which binds RANTES and MIP-1α (Neote et al., 1993, *Cell* 72:415–425), CCR-4, which binds RANTES, MIP-1α, and MCP-1 (Power et al., 1995, *J. Biol. Chem.* 270:19495–19500), and CCR-5, which binds RANTES, MIP-1α, and MIP-1β (Alkhatib et al., 1996, *Science*, in press and Dragic et al., 1996, *Nature* 381:667–674). Erythrocytes possess a receptor (known as the Duffy antigen) which binds both α and β chemokines (Horuk et al., 1994, *J. Biol. Chem.* 269:17730–17733; Neote et al., 1994, *Blood* 84:44–52; and Neote et al., 1993, *J. Biol. Chem.* 268:12247–12249). Thus the sequence and structural homologies evident among chemokines and their receptors allows some overlap in receptor-ligand interactions.

CCR-5 is the major coreceptor for macrophage-tropic strains of HIV-1 (Alkhatib et al., 1996, *Science* 272:1955–1958; Choe et al., 1996, *Cell* 85:1135–1148; Deng et al., 1996, *Nature* 381:661–666; Doranz et al., 1996, *Cell* 85:1149–1158; Dragic et al., 1996, *Nature* 381:667–674). RANTES, MIP-1α, or MIP-1β, the chemokine ligands for this receptor have been shown to block HIV Env-mediated cell fusion directed by CCR-5 (Alkhatib et al., 1996, *Science* 272:1955–1958 and Dragic et al., 1996, *Nature* 381:667–674). Additional support for the role of CCR-5 as an M-tropic HIV-1 cofactor comes from the finding that a 32-base pair deletion in the CCR-5 gene found in three multiply exposed, but uninfected individuals, prevents HIV from infecting macrophages (Liu et al., 1996, *Cell* 86:367–377). However, only three of the 25 uninfected individuals studied had this mutation. This 32-base pair deletion in the CCR-5 gene is found in many (1% uninfected approximately 13% non-risk) caucasians. See also Huang et al., 1996, *Nature Med.* 2:1240–1243; Samson et al., 1996, *Nature* 382:722–725; Dean et al., 1996, *Science* 273:1856–1862; and Michael et al., 1997, *Nature Med.* 3:338–340.

CD4+ T lymphocytes from these individuals, moreover, are not infected by HIV-1 in vitro. A disproportionately high number of these individuals are homozygous for a mutant CC-CKR5 allele that contains a 32 base pair deletion (Dean et al., 1996, *Science* 273:1856–1862).

The V3 loop of gp120 is the major determinant of sensitivity to chemokine inhibition of infection or replication (Cocchi et al., 1996, *Nature Medicine* 2:1244–1247; and Oravecz et al., 1996, *J. Immunol.* 157:1329–1332). Signal transduction through β chemokine receptors is not required for inhibition of HIV infection or replication, since RANTES inhibits HIV-1 infection in the presence of pertussis toxin, an inhibitor of G-protein-mediated signaling pathways (P. M. Murphy 1994, *Ann. Rev. Immunol.* 12:593–633; Bischoff et al., 1993, *Eur. J. Immunol.* 23:761–767; and Simon et al., 1991, *Science* 252:802–807). In addition, mutant chemokine receptors that lack normal function retain the ability to act as HIV coreceptors. For example, deletion of "signalling sequences" have no effect on coreceptor function (Lu et al., 1997, *Proc. Natl. Acad. Sci. USA* 94:6426) and mutant chimeras that do not signal chemotaxis do act as coreceptors (Atchison et al., 1996, *Science* 274:1924). CxC CKR4, a CxC (α) chemokine receptor, has been shown to be a coreceptor involved in infection by laboratory-adapted HIV-1 strains (Fong et al., 1996, *Science* 272:872–877). The α chemokine SDF-1, the ligand for this receptor, has been demonstrated to block infection by T-tropic HIV-1 isolates. CxC CKR4 does not bind the beta chemokines RANTES, MIP-1α, or MIP-1β.

Recently, it has been shown that certain primary, syncytium-inducing/T-tropic isolates use both CC CKR5 and CxC CKR4 as coreceptors and are able to switch between the two. Thus, in the presence of RANTES, MIP-1α and MIP-1β, the chemokine ligands for CCR-5, T-tropic strains are still able to infect cells via the CxC CKR4 coreceptor (Zhang et al., 1996, *Nature* 383:768).

Godiska et al. identified and described the nucleic acid and amino acid sequences of an additional β chemokine designated the macrophage derived chemokine (MDC) (PCT Publication WO 96/40923 dated Dec. 19, 1996, and 1997, *J. Exp. Med.* 185:1595–1604). The PCT publication WO 96/40923 further provides materials and methods for the recombinant production of the chemokine, the purified and isolated chemokine protein, and polypeptide analogues thereof. While the PCT publication WO 96/40923 discloses that a need exists for additional C—C chemokines for use as inhibitors of strains of HIV (see page 4, lines 15–23) and discloses an assay for determining whether MDC has HIV inhibiting effects (see page 17, lines 16–17 and Example 20), the reference fails to teach or provide any evidence that MDC does inhibit HIV proliferation or what strains of HIV MDC would be effective against. There is no enabling disclosure therein of using MDC to treat or prevent HIV infection or disorders stemming therefrom.

Further, PCT Publication WO 96/40923 dated Dec. 19, 1996, states that the established correlation between chemokine expression and inflammatory conditions and disease states provides for diagnostic and prognostic uses for chemokines (see page 5). However, the PCT publication fails to disclose or suggest methods for diagnosis or prognosis of HIV infection using MDC expression. Both of the Godiska et al. references fail to detect MDC expression in unactivated or activated PBMCs.

Klotman et al. (May 4, 1997, Abstract page 40, Conference on Advances in AIDS Vaccine Development, 9th Annual Meeting of the National Cooperative Vaccine Development Group for AIDS) describes a method for producing an anti-HIV-1 factor from cultured, transformed CD8+ cell supernatants. A factor was purified by concentrating cell supernatants and subjecting them to size fractionation, ion exchange and reverse-phase chromatography. The factor is apparently distinct from RANTES, MIP-1α and MIP-1β. No hysical characteristics (e.g., molecular weight, sequence, etc.) of the factor are disclosed.

HIV infection is pandemic and HIV-associated diseases represent a major world health problem. Although considerable effort is being put into the design of effective therapeutics, currently no curative anti-retroviral drugs against AIDS exist. In attempts to develop such drugs, several stages of the HIV life cycle have been considered as targets for therapeutic intervention (Mitsuya et al., 1991, *FASEB J.* 5:2369–2381). Many viral targets for intervention with the HIV life cycle have been suggested, as the prevailing view is that interference with a host cell protein would have deleterious side effects. For example, virally encoded reverse transcriptase has been one focus of drug development. A number of reverse-transcriptase-targeted drugs, including 2', 3'-dideoxynucleoside analogues such as AZT, ddI, ddc, and d4T have been developed which have been shown to been active against HIV (Mitsuya et al., 1991, *Science* 249:1533–1544).

The new treatment regimens for HIV-1 show that a combination of anti-HIV compounds, which target reverse transcriptase (RT), such as azidothymidine (AZT), lamivudine (3TC), dideoxyinosine (ddi), dideoxycytidine (ddc) used in combination with an HIV-1 protease inhibitor have a far greater effect (2 to 3 logs reduction) on viral load compared to AZT alone (about 1 log reduction). For example, impressive results have recently been obtained with a combination of AZT, ddI, 3TC and ritonavir (Perelson et al., 1996, *Science* 15:1582–1586). However, it is likely that long-term use of combinations of these chemicals will lead to toxicity, especially to the bone marrow. Long-term cytotoxic therapy may also lead to suppression of CD8+ T cells, which are essential to the control of HIV, via killer cell activity (Blazevic et al., 1995, *AIDS Res. Hum. Retroviruses* 11:1335–1342) and by the release of factors which inhibit HIV infection or replication, notably the chemokines Rantes, MIP-1α and MIP-1β (Cocchi et al., 1995, *Science* 270:1811–1815). Another major concern in long-term chemical anti-retroviral therapy is the development of HIV mutations with partial or complete resistance (Lange, J. M., 1995, *AIDS Res. Hum. Retroviruses* 10: S77–82). It is thought that such mutations may be an inevitable consequence of anti-viral therapy. The pattern of disappearance of wild-type virus and appearance of mutant virus due to treatment, combined with coincidental decline in CD4+ T cell numbers strongly suggests that, at least with some compounds, the appearance of viral mutants is a major underlying factor in the failure of AIDS therapy.

Attempts are also being made to develop drugs which can inhibit viral entry into the cell, the earliest stage of HIV infection, by focusing on CD4, the cell surface receptor for HIV. Recombinant soluble CD4, for example, has been shown to inhibit infection of CD4+ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). In addition, recombinant soluble CD4 clinical trials have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

The late stages of HIV replication, which involve crucial virus-specific processing of certain viral encoded proteins, have also been suggested as possible anti-HIV drug targets. Late stage processing is dependent on the activity of a viral protease, and drugs are being developed which inhibit this protease (Erickson, J., 1990, Science 249:527–533). The clinical outcome of these candidate drugs is still in question.

Attention is also being given to the development of vaccines for the treatment of HIV infection. The HIV-1 envelope proteins (gp160, gp120, gp41) have been shown to be the major antigens for neutralizing anti-HIV antibodies present in AIDS patients (Barin et al., 1985, Science 228:1094–1096). Thus far, therefore, these proteins seem to be the most promising candidates to act as antigens for anti-HIV vaccine development. Several groups have begun to use various portions of gp160, gp120, and/or gp41 as immunogenic targets for the host immune system. See, for example, Ivanoff et al., U.S. Pat. No. 5,141,867; Saith et al., WO 92/22654; Shafferman, A., WO 91/09872; Formoso et al., WO 90/07119. To this end, vaccines directed against HIV proteins are problematic in that the virus mutates rapidly rendering many of these vaccines ineffective. Clinical results concerning these candidate vaccines, however, still remain far in the future.

Thus, although a great deal of effort is being directed to the design and testing of anti-retroviral drugs, effective, non-toxic treatments are still needed.

Citation of a reference hereinabove shall not be construed as an admission that such reference is prior art to the present invention.

3. SUMMARY OF THE INVENTION

The present invention relates to prophylactic and therapeutic methods and compositions based on MDC proteins, nucleic acids, derivatives or analogues thereof that inhibit replication and/or infection of a lentivirus, particularly an immunodeficiency virus in vitro or in vivo, decrease viral load, and/or treating or preventing diseases and disorders associated with infection of a lentivirus, particularly an immunodeficiency virus. In specific embodiments, the lentivirus inhibited by the methods and compositions of the invention is HIV.

The present invention also relates to therapeutic compositions based on MDC and nucleic acids encoding MDC. Therapeutic compounds of the invention include, but are not limited to, MDC, nucleic acids encoding MDC, and derivatives (including, but not limited to, fragments and chimerics) and analogues thereof, that are effective at inhibiting replication or infection by an immunodeficiency virus.

The invention further relates to therapeutic methods for treatment and prevention of diseases and disorders associated with infection with a lentivirus, in particular an immunodeficiency virus, in particular HIV infection, by administering a therapeutic composition of the invention.

The invention further relates to methods for prognosis of lentivirus infection, in particular HIV infection, using MDC as a prognostic indicator.

The invention further provides MDC proteins, and nucleic acids encoding such proteins, that have amino-terminal sequences that differ from other molecular forms of MDC. Recombinant host cells and methods of production are also provided.

4. DESCRIPTION OF FIGURES

FIG. 1. Reversed phase HPLC profile of MDC purified from serum free culture supernatant of F3b clone 19 cells. A portion of the peak fraction was analyzed by SDS-PAGE and stained with coomassie blue (inset).

Figure 2:
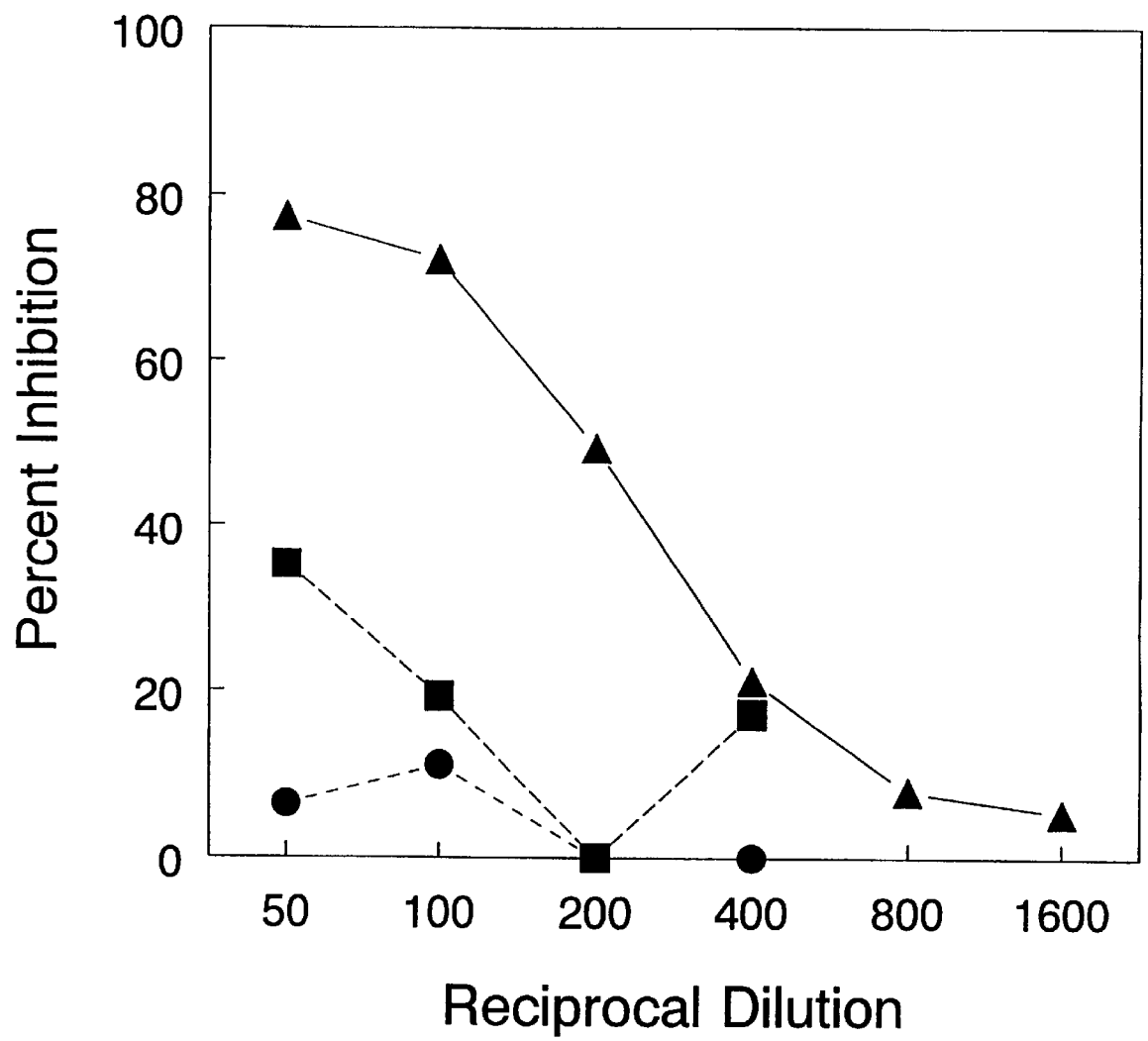

FIG. 2. HIV-1 suppressive activity of purified MDC. PBMCs ($2 \times 10^5$) from normal donors, previously activated with PHA and depleted of CD8+ cells, were infected with 50 $TCID_{50}$ of HIV-$1_{IIIB}$ for 3 hrs at 37° C. The cells were then washed and treated with different dilutions of a reversed phase HPLC fraction containing purified MDC (fraction 27, triangles) or flanking fractions (fractions 26, circles; and 28, squares). On day 2 post-infection, cultures were fed with fresh medium containing corresponding dilutions of each fraction. Virus replication was determined by HIV-1 p24 ELISA of the culture medium on day 5. Percent inhibition of infection was calculated based on the level of infection in control assays carried out in the absence of test sample. The concentration of MDC present in fraction 27 was 10 μg/ml as determined by amino acid analysis. The results represent a typical experiment repeated several times with similar results.

Figure 3A:
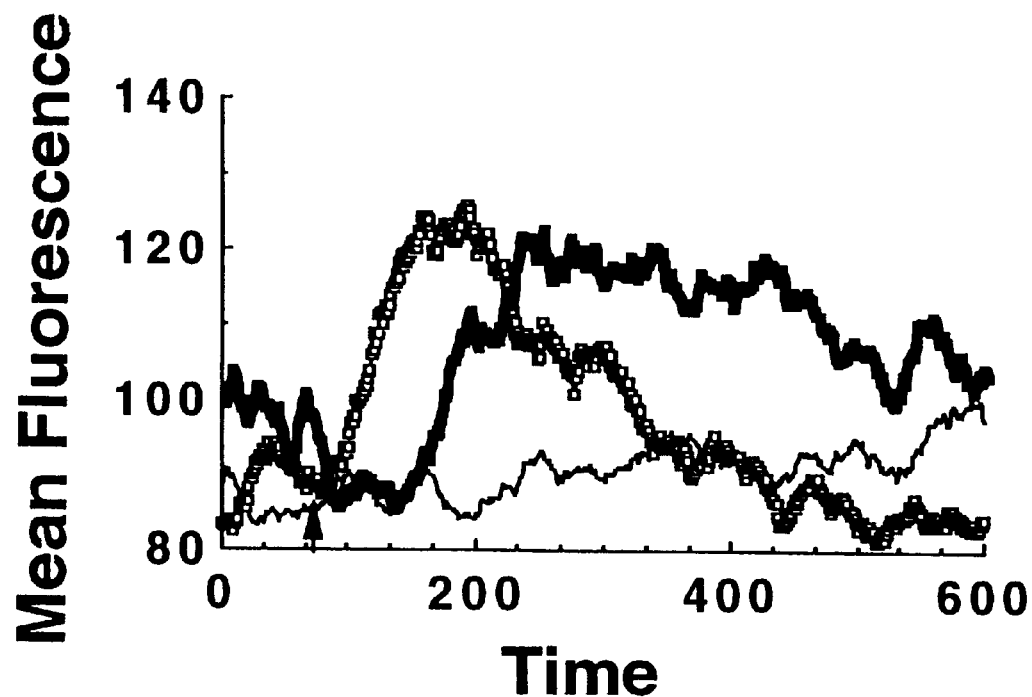
Figure 3B:
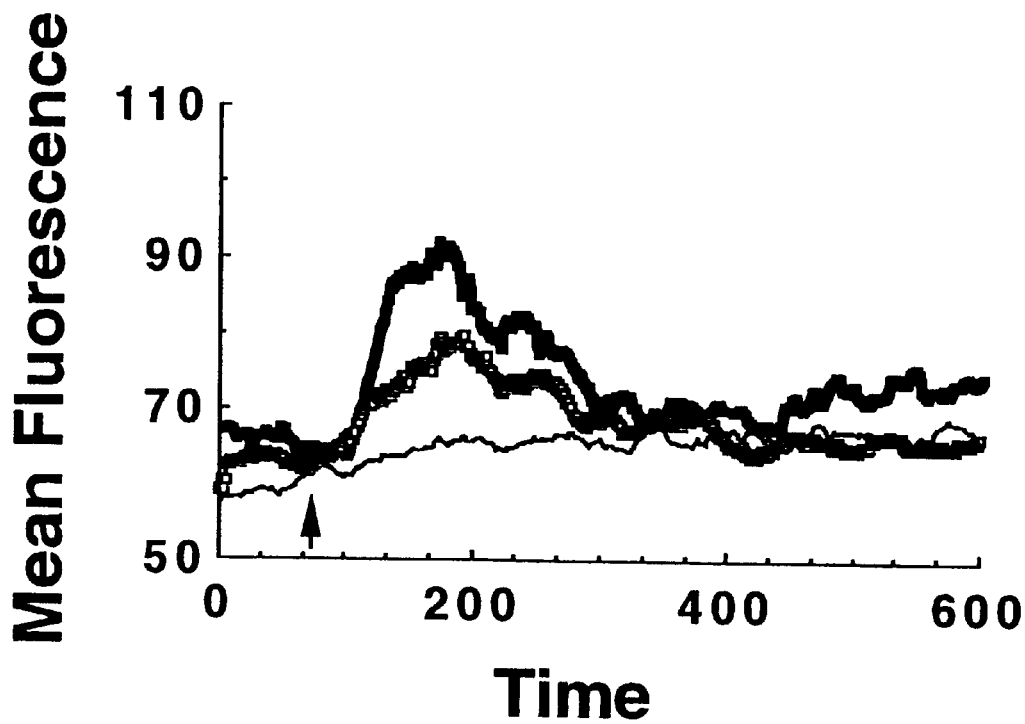

FIGS. 3A and 3B. MDC-induced increases in intracellular calcium in CD8-depleted and unfractionated PBMCs. (3A) PBMCs were depleted of CD8+ cells and cultured as described for the infectivity assay (see Section 8). The cells were stimulated with a 3nM concentration of SDF-1β (thick line) or MDC purified by reversed phase HPLC (squares) or incubated with phosphate-buffered saline (thin line). (3B) PBMCs were activated with 5 μg/ml PHA and 10 ng/ml IL-2 for 72 hours and cultured in the same concentration of IL-2 for 14 days. The cells were then assayed as described (see Section 9) for changes in cytosolic calcium in response to a 3 nM concentration of RANTES (thick line) or MDC (squares). In all experiments control assays were carried out with phosphate buffered saline (thin line). Chemokine or control additions were made at the time marked by the arrow. Data were acquired for at least 3 minutes. One time unit is equivalent to 0.2 seconds.

Figure 4:
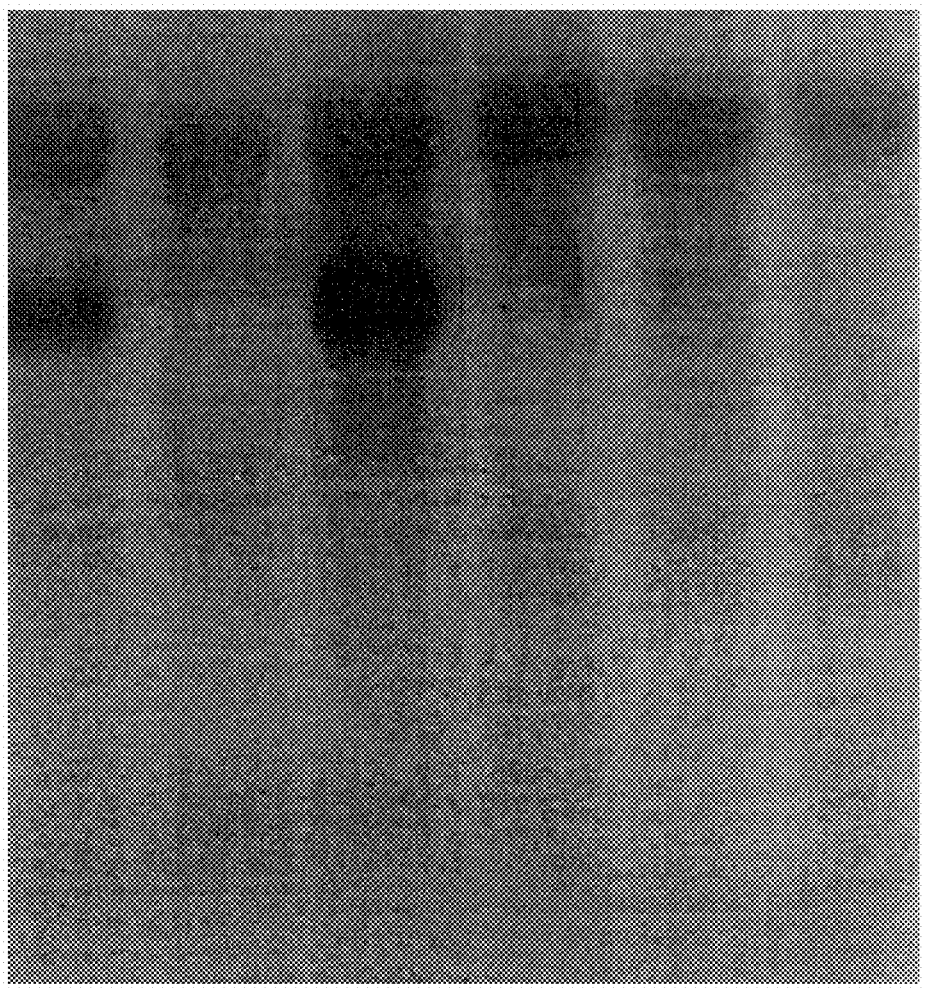

FIG. 4. Northern blot analysis of MDC expression in immortalized T cell lines and primary PBMCs. The experiments were carried out as described in Section 10. Lane 1, activated PBMCs; lane 2, resting PBMCs; lane 3, F3b clone 19; lane 4, HUT 78 plus IL-2; lane 5, HUT 78; lane 6, PM1.

FIGS. 5A and 5B. The nucleotide and amino acid sequences of MDC. (5A) depicts the nucleotide sequence of MDC (SEQ ID NO:1), with the coding region indicated by the appearance of the amino acid sequence in the line below; and (5B) depicts the amino acid of MDC (SEQ ID NO:2) from GenBank accession no. U83171 (Godiska et al., 1997, J. Exp. Med. 185:1595–1604).

5. DETAILED DESCRIPTION OF THE INVENTION

The present invention relates to therapeutic compositions comprising MDC, nucleic acids encoding MDC, derivatives and/or analogues thereof, and nucleic acids encoding the same, that are effective at inhibiting replication and/or infection of a lentivirus, in particular an immunodeficiency virus, in vitro or in vivo, decreasing viral load, and/or treating or preventing diseases and disorders associated with human infection with a lentivirus. The lentivirus, in particular an immunodeficiency virus, can be, but is not limited to, HIV, simian immunodeficiency virus, feline immunodeficiency virus, and bovine immunodeficiency virus, and is most preferably HIV.

The invention also relates to therapeutic methods and compositions for the treatment and prevention of diseases and disorders associated with infection by lentiviruses, preferably immunodeficiency viruses, more preferably HIV infections, by administration of MDC preparations. The invention provides for treatment of a lentivirus infection, in particular HIV infection, by administration of therapeutic compositions of the invention. Therapeutic compounds of the invention include MDC, nucleic acids encoding MDC, and related therapeutically and prophylactically effective derivatives and analogues thereof and nucleic acids encoding the same.

The pharmaceutical compositions of the invention optionally further comprise a therapeutically or prophylactically effective amount of another anti-HIV agent.

The invention also provides in vitro and in vivo assays for assessing the efficacy of therapeutics of the invention for treatment or prevention of infection with a lentivirus, in particular an immunodeficiency virus, particularly HIV infection.

The invention further relates to methods for treating or preventing lentivirus infection, particularly immunodeficiency virus infection, in particular HIV, in mammals, including humans, by administering the therapeutic compositions of the invention. Methods of administration of the therapeutics of the invention for treatment or prevention of lentivirus infection are also provided.

Additionally, the invention provides methods for prognosis of a lentivirus infection, in particular HIV infection,using MDC as a prognostic indicator. In particular, asymptomatic individuals with a lentivirus infection are believed to have increased expression, relative to uninfected individuals, of MDC by a T cell subset (in particular $CD8^+$ T cells) of peripheral blood mononuclear cells (PBMCs). It is expected that a decrease in the level of expression of MDC in these T cells is indicative of progression from asymptomatic toward symptomatic infection. Loss of expression of MDC by $CD8^+$ T cells indicates progression toward symptomatic lentivirus infection, in particular symptomatic HIV infection such as AIDS. The methods of prognosis of lentivirus infection may use immunological or nucleic acid hybridization techniques for detecting MDC protein and RNA expression, respectively, as the prognostic indicator.

For clarity of disclosure, and not by way of limitation, the detailed description of the invention is divided into the subsections which follow.

5.1. MDC, Derivatives and Analogues

The present invention relates to macrophage derived chemokine (MDC), which the present inventors have found suppresses the infection of lentiviruses, in particular HIV.

The invention provides pharmaceutical compositions comprising the β chemokine MDC, nucleic acids encoding chemokines, derivatives (e.g., fragments) or analogues thereof, or nucleic acids encoding the derivatives or analogues, that have activity in the treatment and prevention of disorders associated with lentivirus infection, preferably immunodeficiency infection, more preferably HIV infection. In a specific embodiment, the compounds of the invention inhibits lentivirus infection or replication, in particular HIV infection or replication.

In a specific embodiment, the MDC provided by the invention has the amino terminal sequence Tyr-Gly-Ala-Asn-Met-Glu-Asp-Ser-Val-Cys-Cys-Arg-Asp-Tyr-Val-Arg-Tyr-Arg-Leu (amino acids 3–21 of SEQ ID NO:2), and a full length sequence of amino acid numbers 3–69 of SEQ ID NO:2. In another specific embodiment, the MDC provided by the invention has the amino-terminal sequence Pro-Tyr-Gly-Ala-Asn-Met-Glu-Asp-Ser-Val-Cys-Cys-Arg (amino acids 2–14 of SEQ ID NO:2), and a full length sequence of amino acid numbers 2–69 of SEQ ID NO:2.

In a specific embodiment, the invention relates to MDC derivatives and analogues, or nucleic acids encoding MDC derivatives and analogues, that comprise, or alternatively consist of an amino acid sequence capable of binding to a chemokine receptor.

In another specific embodiment, the invention relates to MDC derivatives and analogues, that comprise, or alternatively consist of an amino acid sequence capable of binding to an anti-MDC antibody.

In a specific embodiment of the invention, proteins consisting of or alternatively comprising a fragment of MDC consisting of at least 5 (continuous) amino acids of the chemokine is provided. In other embodiments, the fragment consists of at least 6, 7, 8, 9, 10, 15, 20, 30, 40, 50, or 60 amino acids of the chemokine. In specific embodiments, such fragments are not larger than 10, 20, 30, 40, 50, 60 or 70 amino acids. Derivatives or analogues of a chemokine include, but are not limited to, those molecules exhibiting antiviral activity and that comprise regions that are substantially homologous to a chemokine or fragment thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding chemokine sequence, under high stringency, moderately high stringency, or low stringency conditions. In a specific embodiment, the chemokine derivative retains the antigenicity (ability to bind to an anti-chemokine antibody) or immunogenicity of the chemokine. Fragments and other derivatives of a chemokine that retain the ability to bind to a chemokine receptor are preferred.

By way of example and not limitation, procedures using conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art.

By way of example and not limitation, procedures using conditions of high stringency are as follows:

prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

By way of example and not limitation, procedures using conditions of moderately high stringency are as follows: filters containing DNA are pretreated for 6 hours to overnight at 55° C. in buffer composed of 6×SSC, 5× Denhart's 0.5% SDS, 100 mg/mL salmon sperm DNA. Hybridizations are carried out in the same solution upon adding 5–20×10$^6$ cpm of $^{32}$P-labeled probe and incubated 8–48 hours at 55° C. Washing of filters is done at 60° C. in 1×SSC, 0.1% SDS, with two exchanges after 30 minutes. Other conditions for moderately high stringency screening are known in the art. For further guidance regarding hybridization conditions see, for example, Sambrook et al., 1989, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.

The invention also relates to MDC derivatives or analogues made by altering the chemokine sequence by substitutions, additions or deletions that provide molecules with anti-viral activity (e.g., inhibit infection or replication of an immunodeficiency virus, preferably HIV) or demonstrate the ability to bind to a chemokine receptor and/or the ability to bind to a chemokine receptor and not activate the receptor. Thus, the MDC derivatives include polypeptides containing, as a primary amino acid sequence, all or part of the MDC amino acid sequence including altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such chemokine derivatives can be made either by chemical peptide synthesis or by recombinant production from nucleic acid encoding the chemokine which nucleic acid has been mutated. Any technique for mutagenesis known in the art can be used, including, but not limited to, chemical mutagenesis, in vitro site-directed mutagenesis (Hutchinson et al., 1978, *J. Biol. Chem* 253:6551), use of TAB® linkers (Pharmacia), PCR with mutation-containing primers, etc.

Furthermore, if desired, nonclassical amino acids or chemical amino acid analogues can be introduced as a substitution or addition into the chemokine, derivative or analogue. Non-classical amino acids include, but are not limited to, the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

Also included within the scope of the invention are MDC proteins, derivatives, and analogues which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the MDC proteins, derivatives, or analogues are acetylated at the N-terminus and/or amidated at the C-terminus. Any of numerous chemical modifications may be carried out by known techniques, including, but not limited to, acetylation, formylation, oxidation, reduction, metabolic synthesis in the presence of tunicamycin, etc. These modifications may serve to increase the stability, bioavailability and/or inhibitory action of the peptides of the invention.

Any of the MDC proteins, derivatives or analogues described above may, additionally, have a non-peptide macromolecular carrier group covalently attached to its amino and/or carboxy termini. Such macromolecular carrier groups may include, for example, lipid-fatty acid conjugates or carbohydrates.

Antiviral activity of MDC proteins, nucleic acids encoding MDC proteins, or derivatives (including fragments and chimeric proteins) or analogues thereof, for treatment or prevention of HIV infection can be demonstrated by any of the methods disclosed in Section 5.2, 7, 8, 9 and 10, infra or known to one skilled in the art.

5.1.1. Preparation of MDC Proteins, Derivatives and Analogues

The β chemokine MDC, and derivatives or analogues thereof can be purified from biological tissue or cell culture, or produced by recombinant or synthetic techniques known in the art.

Native chemokine preparations can be obtained from a variety of sources. Standard methods of protein purification may be used to isolate and purify, or partially purify, chemokines from any source known to contain or produce the desired chemokine, e.g., MDC may be isolated from sources such as cell supernatants of transformed CD8$^+$ T cells infected with HIV-1, macrophages, dendritic cells, or activated PBMCs. MDC may also be isolated from human tissue sources such as the thymus, spleen, lung or small intestine. Such standard protein purification techniques include, but are not limited to, chromatography (e.g., ion exchange, affinity, gel filtration/molecular exclusion chromatography and reversed phase high performance liquid chromatography (RP-HPLC)), centrifugation, differential solubility, and electrophoresis (for a review of protein purification techniques, see, Scopes, Protein Purification; Principles and Procedure, 2nd Ed., C. R. Cantor, Editor, Springer Verlag, New York, N.Y. (1987), and Parvez et al., Progress in HPLC, Vol. 1, Science Press, (1985) Utrecht, The Netherlands).

Recombinant expression techniques can be applied to obtain the MDC proteins, derivatives, and analogues of the invention (see, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleotide sequence of MDC has been published (PCT Publication WO 96/40923 dated Dec. 19, 1996; Godiska et al., 1997, *J. Exp. Med.* 185(9):1595–1604), and is set forth in FIG. 5 (SEQ ID NO:1). An MDC clone can be isolated using well-known techniques in the art, such as by screening a library, chemical synthesis, or polymerase chain reaction (PCR). Cloned chemokine gene sequences can be modified by any of numerous strategies known in the art.

To produce a recombinant MDC protein, derivative or analogue, a nucleic acid sequence encoding the MDC protein, derivative or analogue is operatively linked to a promoter such that the MDC protein, derivative, or analogue is produced from said sequence. For example, a vector can be introduced into a cell, within which cell the vector or a portion thereof is expressed, producing MDC or a portion thereof. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art.

In a specific embodiment, a method for the production of MDC comprises: (a) culturing a host cell containing a recombinant expression vector, said vector comprising a nucleotide sequence encoding MDC under conditions such that MDC is expressed by the cell; and (b) recovering MDC expressed by the cell; in which the cell processes MDC to produce an amino-terminal Tyr or Pro.

A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities and depending on the host-vector system utilized, any one of a number of suitable transcription and translation elements may be used.

Expression of an MDC protein, derivative, or analogue may be controlled by any promoter/enhancer element known in the art. Such promoters include, but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42); prokaryotic expression vectors such as the β-lactamase promoter (Villa-Kamaroff et al., 1978, *Proc. Natl. Acad. Sci. USA* 75:3727–3731), or the tac promoter (DeBoer et al., 1983, *Proc. Natl. Acad. Sci. USA* 80:21–25); see also "Useful proteins from recombinant bacteria" in *Scientific American*, 1980, 242:74–94; plant expression vectors comprising the nopaline synthetase promoter region (Herrera-Estrella et al., *Nature* 303:209–213) or the cauliflower mosaic virus 35S RNA promoter (Gardner et al., 1981, *Nucl. Acids Res.* 9:2871), and the promoter of the photosynthetic enzyme ribulose biphosphate carboxylase (Herrera-Estrella et al., 1984, *Nature* 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58; alpha 1-antitrypsin gene control region which is active in the liver (Kelsey et al., 1987, *Genes and Devel.* 1:161–171), beta-globin gene control region which is active in myeloid cells (Mogram et al., 1985, *Nature* 315:338–340; Kollias et al., 1986, *Cell* 46:89–94; myelin basic protein gene control region which is active in oligodendrocyte cells in the brain (Readhead et al., 1987, *Cell* 48:703–712); myosin light chain-2 gene control region which is active in skeletal muscle (Sani, 1985, *Nature* 314:283–286), and gonadotropic releasing hormone gene control region which is active in the hypothalamus (Mason et al., 1986, *Science* 234:1372–1378). The promoter element which is operatively linked to the nucleic acid encoding an MDC protein, derivative or analogue can also be a bacteriophage promoter with the source of the bacteriophage RNA polymerase expressed from a gene for the RNA polymerase on a separate plasmid, e.g., under the control of an inducible promoter, for example, the nucleic acid encoding chemokine, derivative, or analogue, operatively linked to the T7 RNA polymerase promoter with a separate plasmid encoding the T7 RNA polymerase.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered chemokine, derivative or analogue may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast or insect cells will produce a glycosylated product. Expression in mammalian cells can be used to ensure "native" glycosylation of a heterologous protein. Furthermore, different vector/host expression systems may effect processing reactions to different extents.

Applicants have found that human cell lines express a mature MDC protein with the N-terminal amino acid of Tyr (at amino acid position 3 of SEQ ID NO:2) or Pro (at amino acid position 2 of SEQ ID NO:2). Accordingly, in a specific embodiment, the invention provides a method of producing MDC proteins with the amino-terminal sequences Tyr-Gly-Ala-Asn-Met-Glu-Asp-Ser-Val-Cys-Cys-Arg-Asp-Tyr-Val-Arg-Tyr-Arg-Leu (amino acids 3–21 of SEQ ID NO:2) or Pro-Tyr-Gly-Ala-Asn-Met-Glu-Asp-Ser-Val-Cys-Cys-Arg (amino acids 2–14 of SEQ ID NO:2) by expressing nucleic acids encoding MDC in human cells, or other host cells (e.g., non-CHO cells) that process the MDC precursor molecule (containing a leader sequence) so as to produce MDC proteins with such amino-terminal sequences.

In a specific embodiment, the MDC protein can be expressed in mammalian cells, e.g., other than CHO cells, or insect cells by expressing a nucleic acid comprising at least the coding nucleotide sequence of SEQ ID NO:1. In a more specific embodiment, a non-CHO host cell is used that contains a recombinant expression vector, said vector comprising a nucleotide sequence encoding MDC, operably linked to a non-MDC promoter.

In another specific embodiment, the MDC protein can be expressed in mammalian or insect cell lines using modified MDC encoding nucleotide sequences. For example, the modified nucleotide sequence can encode MDC proteins that contain the leader sequence of SEQ ID NO:1 (amino acids nos. −24 to −1), but in which the nucleotide sequence codon encoding the first amino acid (Gly) or the first two codons encoding the first and second amino acids (Gly-Pro), respectively, have been deleted.

In a specific embodiment, expression of the MDC protein in bacterial or prokaryotic cell lines can be accomplished by expressing a nucleic acid comprising the coding nucleotide sequence of SEQ ID NO:1, followed by post-purification cleavage to remove the leader peptide and amino acid number 1 or numbers 1–2 of SEQ ID NO:2. By way of example, an enzyme cleavage recognition site (e.g., Factor X) may be introduced subsequent to amino acid numbers 1 or 2 of SEQ ID NO:2. Alternatively, the nucleotide sequence encoding only the mature MDC proteins, without the nucleotide sequence encoding the leader sequence and amino acid number 1 or numbers 1–2, can be expressed. In this case, a codon for methionine is positioned 5' to the first codon of mature MDC nucleotide sequence, the codon for the Pro at amino acid number 2 of SEQ ID NO:1 or for the Tyr at amino acid number 3 of SEQ ID NO:1. Such a construct may also be used for expression in nonmicrobial systems.

In a specific embodiment, a recombinant expression vector comprises a nucleotide sequence encoding an MDC protein, the amino acid sequence of which consists of amino acid numbers 2–69 of SEQ ID NO:2, without a leader sequence, operably linked to a non-MDC promoter.

In another specific embodiment, a recombinant expression vector comprises a nucleotide sequence encoding an MDC protein, the amino acid sequence of which consists of amino acid numbers 3–69 of SEQ ID NO:2, without a leader sequence, operably linked to a non-MDC promoter.

In another specific embodiment, a recombinant expression vector comprises a nucleotide sequence encoding an MDC protein, the amino acid sequence of which consists of the amino acid sequence Tyr-Gly-Ala-Asn-Met-Glu-Asp-Ser-Val-Cys-Cys-Arg-Asp-Tyr-Val-Arg-Tyr-Arg-Leu (amino acids 3–21 of SEQ ID NO:2) without a leader sequence, operably linked to a non-MDC promoter.

In yet another specific embodiment, a recombinant expression vector comprises a nucleotide sequence encoding an MDC protein, the amino acid sequence of which consists of the amino acid sequence Pro-Tyr-Gly-Ala-Asn-Met-Glu-Asp-Ser-Val-Cys-Cys-Arg (amino acids 2–14 of SEQ ID NO:2) without a leader sequence, operably linked to a non-MDC promoter.

The MDC-encoding nucleic acid sequence can be mutated in vitro or in vivo, to create and/or destroy translation, initiation, and/or termination sequences, or to create variations in coding regions. Any technique for mutagenesis known in the art can be used, including, but not limited to, in vitro site-directed mutagenesis (Hutchinson et al., 1978, *J. Biol. Chem* 253:6551), use of TAB® linkers (Pharmacia), mutation-containing PCR primers, etc.

The experimentation involved in mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

In other specific embodiments, the MDC derivative or analogue may be expressed as a fusion, or chimeric protein product (comprising the protein, fragment, analogue, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

In addition, MDC proteins, derivatives (including fragments and chimeric proteins), and analogues can be chemically synthesized. See, e.g., Clark-Lewis et al., 1991, *Biochem.* 30:3128–3135 and Merrifield, 1963, *J. Amer. Chem. Soc.* 85:2149–2156. For example, MDC, derivatives and analogues can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). MDC, derivatives and analogues that are proteins can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49).

The MDC proteins, derivatives, or analogues of the invention may be synthesized in their entirety by the sequential addition of amino acid residues or alternatively as fragment subcomponents which may be combined using techniques well known in the art, such as, for example, fragment condensation (Shin et al., 1992, *Biosci. Biotech. Biochem.* 56:404–408; Nyfeler et al., 1992, Peptides, Proc. 12th Amer. Pep. Soc., Smith and Rivier (eds), Leiden, pp 661–35 663); and Nokihara et al., 1990, Protein Research Foundation, Yanaihara (ed), Osaka, pp 315–320).

In a less preferred embodiment, MDC derivatives can be obtained by proteolysis of the protein followed by purification using standard methods such as those described above (e.g., immunoaffinity purification).

5.2. Assays for Receptor Binding and Inhibition of Viral Infection or Replication by MDC Proteins, Derivatives and Analogues The ability of MDC proteins or the derivatives or analogues thereof to bind chemokine receptors and thereby interfere with viral infection or replication can be assayed by various methods. In particular, known chemokine receptors can be assayed for the ability to be bound by MDC, or derivatives or analogues thereof.

In a preferred embodiment, the MDC derivatives (including fragments and chimeric proteins) or analogues, bind protein sequences contained in the extracellular domain of a chemokine receptor. Binding can be assayed by means well-known in the art. For example, bioassays may be performed in which cells known to be expressing an MDC receptor are exposed to the MDC derivative or analogue to be tested and assayed for a known effect (e.g., signal transduction, chemotaxis). Alternatively, MDC proteins, derivatives or analogues can be tested for the ability to bind MDC receptors by procedures, including, but not limited to, protein affinity chromatography, affinity blotting, immunoprecipitation, flow cytometry, cross-linking, and library based methods such as protein probing, phage display, and the two-hybrid system (see, generally, Phizicky et al., 1995, *Microbiol.* Rev. 59:94–123). Further, where DNA encoding a chemokine receptor has been identified, this sequence may be routinely manipulated in known assays to identify chemokine derivatives or analogues which bind to the extracellular domain of the receptor. Such assays include, but are limited to, in vitro cell aggregation and interaction trap assays. Nucleic acids encoding CCR-1 (Neote et al., 1993, *Cell* 72:415–425); CCR-2A and CCR-2B (Chavo et al., 1994, *Proc. Natl. Acad. Sci.* 91:2752–2756); CCR-3 (Daugherty et al., 1996, *J. Exp. Med.* 183:2349–2354 and Ponath et al., 1996, *J. Exp. Med.* 183:1–12); CCR-4 (Power et al., 1995, *J. Biol. Chem.* 270:19495–19500); CCR-5 (Samson et al., 1996, *Biochemistry* 35:3362–3367); CxC CKR4 (Feng et al., 1996, *Science* 272:872–877); IL-8RA and IL-8RB (Kunz et al., 1991, *J. Biol. Chem.* 267:9101–9106 and Gerard et al., 1994, *Corr. Opin. Immunol.* 6:140–145); Duffy antigen (Horuk et al., 1994, *J. Biol. Chem.* 269:1770–1773; Neote et al., 1994, *Blood* 84:44–52; and Neote et al., 1993, *J. Biol. Chem.* 268:12247–12249); Mig receptor and γIP-10 receptor (Loestcher et al., 1996, *J. Exp. Med.* 184(3):963–969); I309 receptor (Tiffany et al., 1997, *J. Exp. Med.*, in press); and chemokine receptor/HIV coreceptor (Liao et al., 1997, *J. Exp. Med.* 185:2015) have been isolated and cloned.

High throughput screening for chemokine, derivative or analogue receptor binding may be performed by methods known in the art, including, but not limited to, flow cytometry. According to this method, cells that express human CD4 and one of the HIV co-receptors (e.g., CC CKR-5, CxC CKR4, etc.) are treated with biotinylated MDC, derivative, or analogue and cell surface binding to each cell type is detected with an avidin FITC conjugate. Alternatively, other methods for labeling or detecting binding of the chemokine, derivative or analogue, such as antibodies, may be used. The same flow cytometry system may be used to assess receptor binding specificity, by testing for competitive binding between the chemokine, derivative or analogue and known ligands.

The antiviral activity exhibited by the MDC protein, derivative and/or analogue of the invention may be measured, for example, by easily performed in vitro assays, which can test the compound's ability to inhibit syncytia formation or to inhibit infection by cell-free virus and assess the effects of the compound on cell proliferation and viability.

In one embodiment, a cell fusion assay is used to test the ability of chemokine, derivative or analogue, to inhibit HIV-induced syncytia formation in vitro. Such an assay involves culturing uninfected $CD4^+$ cells in the presence of chronically HIV-infected cells and the composition containing a MDC protein, derivative or analogue to be assayed. For each, a range of concentrations may be tested. This range should include a control culture wherein no MDC protein, derivative and/or analogue has been added. Standard conditions for culturing, well known to those of ordinary skill in the art, are used. After incubation for an appropriate period, such as, for example, 24 hours at 37° C., the culture is examined microscopically for the presence of multinucleated giant cells, which are indicative of cell fusion and syncytia formation.

In one embodiment, an in vitro cell-free infectivity assay is performed using primary macrophages and the macrophage-tropic isolate $HIV-1_{BaL}$ or any other primary macrophage-trophic isolate, the first described macrophage-tropic HIV-1 isolate (see, Gartner et al., 1986, *Science* 233:215) (see Section 7 infra). According to this assay, primary macrophage cells isolated according to methods known in the art are infected with $HIV-1_{BaL}$ that has been propagated and maintained only in primary macrophages. The input immunodeficiency virus is incubated with primary macrophages in the presence of concentrations of the MDC protein, derivative, or analogue to be tested. After a defined period of infection, unbound virus is removed by washing, and the cells are placed in culture. The level of virus replication in this assay may be assessed by techniques known in the art, including, but not limited to, measuring reverse transcriptase (RT) levels, or the release of extracellular p24 core antigen at different days post-infection. A constant level of inhibition of viral infection or replication is determined by measuring output HIV p24 levels (or another indicator of viral infection or replication, such as for example, RT) relative to control assays performed in the absence of the MDC protein, derivative or analogue. Preferably, the MDC protein, derivative or analogue reduces levels of virus, as measured by, for example, p24, by $\geq 50\%$ relative to control assays carried out in the absence of test compound. The presence of p24 may be determined using methods known in the art, such as commercially available enzyme-linked immunosorbent assays (Coulter, Hialeah, Fla.; Abbott Laboratories, Hvalstad, Norway). Alternatively, RT activity may be tested by monitoring cell-free supernatant using standard techniques such as those described by, for example, Goff et al. (Goff et al., 1981, *J. Virol.* 38:239–248) and Willey et al. (Willey et al., 1988, *J. Virol.* 62:139–147).

In a preferred embodiment, an in vitro cell-free infectivity assay is performed using activated primary $CD4^+$ peripheral blood mononuclear cells (PBMCs) that have been isolated according to methods known in the art; such as for example, (+) or (−) selection by immunomagnetic beads (Dynal A. S., Norway) and Ficoll gradient centrifugation. Techniques for activating primary PBMC with such compounds as phytohemagglutinin (PHA) or the monoclonal antibody OKT3 in concert with IL-2 are also known in the art (see, e.g., Cocchi et al., 1995, *Science* 270:1811–1815). The activated primary PBMC are incubated with 10–50 $TCID_{50}$ (half-maximal tissue-culture infectious dose) primary syncytia-inducing or non-syncytia-inducing, T-tropic, viral stocks such as those that can be obtained from the NIH AIDS Research and Reference Reagent Program or isolated according to methods known in the art, such as for example, that described in Section 8. Primary virus stocks may also be generated from lymph node T cells (via lymph node aspirate or biopsy). The procedure for isolating virus from lymph node material is the same as that used to isolate virus from PBMCs.

As above, the input immunodeficiency virus is incubated with target cells in the presence of various quantities of the test MDC protein, derivative, or analogue to be tested. After a defined period of infection, unbound virus is removed by washing, and the cells are placed in culture. As above, the level of virus replication in this assay may be assessed by techniques known in the art, including, but not limited to, measuring reverse transcriptase levels or the release of extracellular p24 core antigen at different days post-infection. A constant level of inhibition of viral infection or replication is determined by measuring output HIV p24 levels (or another indicator) relative to control assays performed in the absence of the MDC protein, derivative or analogue. Preferably, the MDC protein, derivative or analogue reduces levels of virus, as measured by, for example, p24, by $\geq 50\%$ relative to control assays carried out in the absence of test compound.

In another embodiment, an assay is performed using cells from $HIV^+$ individuals. According to this assay, $HIV^+$ $CD4^+$ peripheral blood cells are recovered from an infected individual using techniques known in the art and incubated in the presence and absence of test chemokine, derivative or analogue. Optionally, the cells are co-cultured with uninfected allogeneic $CD4^+$ PBMCs. According to this assay, the input immunodeficiency virus is incubated with target cells in the presence of various concentrations of the test MDC protein, derivative, or analogue that are maintained throughout culture. Culture supernatant samples are removed periodically (every 1–3 days) and tested for virus expression by techniques known in the art, such as by measuring the release of extracellular p24 core antigen, or another indicator of viral infection or replication, at different days post-infection. Virus is usually detected by day 7 of culturing. A constant level of inhibition of viral infection or replication is determined relative to control assays performed in the absence of the chemokine, derivative or analogue. For many individuals with advanced infection, $CD4^+$ cell levels are very low. In these cases, $CD4^+$ cells isolated from the $HIV^+$ individual are optionally incubated with uninfected $CD4^+$ target cells. This assay models the rapid viral replication and cytopathic effects contributing to the loss of $CD4^+$ cells in vivo by utilizing primary target cells and primary viral isolates and is exemplified in Section 9.

In another embodiment, MDC protein(s), derivatives and/or analogue(s) are identified by their ability to inhibit the isolation of primary immunodeficiency virus isolates from primary target cells removed from an infected individual. According to this embodiment, $CD4^+$ target cells isolated from an $HIV^+$ individual using techniques known in the art are exposed to one or more MDC proteins, derivatives, and/or analogues and known techniques, such as those described infra, are applied to isolate the virus from the cells. In a preferred embodiment, these MDC proteins, derivatives and/or analogues are known or indicated by the in vitro assays described herein to inhibit the infection or replication of one or more HIV-1 strains. Parallel control experiments are performed in which the same virus isolation technique is performed in the absence of MDC proteins, derivatives, and/or analogues. An inability or reduced ability to isolate immunodeficiency virus in the test samples, but not the control sample indicates that the primary immunodeficiency virus isolates are sensitive to the test MDC proteins, derivatives, and/or analogues.

The MDC protein, derivative, or analogue compositions may then be combined with suitable pharmaceutically acceptable carriers and administered by techniques known in the art, such as those described in Section 5.6 infra.

Techniques known in the art may be applied to formulate compositions displaying minimal toxicity. For each in vitro test of chemokines, derivatives and/or analogues of the invention, it is preferable to determine the effects on cell proliferation and viability. Methods for assessing effects of the compounds tested on cell proliferation include, but are not limited to, assaying for thymidine uptake and counting cells (using, for example, a hemocytometer or flow cytometer). Methods for assessing cell viability include, but are not limited to, trypan blue dye exclusion. In a specific embodiment, an assay is performed in which the proliferative response of stimulated target cells to a range of concentrations of the test composition(s) is assessed by monitoring $[^3H]$-Thymidine incorporation (See Section 10).

Other methods for assaying the antiviral activity of MDC proteins, derivatives and/or analogues will be known to the skilled artisan and are within the scope of the invention.

The assays described herein may be applied to routinely predict which MDC proteins, derivative or analogue will display an antiviral effect in vivo and the optimal concentration for doing so. MDC proteins, derivatives, and analogues displaying anti-viral activity are optionally combined.

The invention provides for treatment or prevention of diseases and disorders associated with infection by a lentivirus, in particular an immunodeficiency virus, particularly HIV, by administration of a therapeutic compound (termed herein "Therapeutic"). Such "Therapeutics" include, but are not limited to: MDC proteins and therapeutically and prophylactically effective MDC derivatives and/or analogues, i.e., those derivatives and analogues which prevent or treat HIV infection (e.g., as demonstrated in vitro assays described herein), as well as nucleic acids encoding such MDC proteins, derivatives and analogues thereof.

The Therapeutics of the invention can also be tested in vivo for toxicity and/or the desired therapeutic or prophylactic activity. For example, such compounds can be tested in suitable animal models including, but not limited to, rats, mice, chickens, cows, sheep, dogs, cats, monkeys, apes, rabbits, etc. For in vivo testing, prior to administration to humans, any animal model system known in the art may be used.

5.3. Therapeutic Uses

The invention provides for treatment or prevention of diseases and disorders associated with infection by a lentivirus, in particular an immunodeficiency virus, particularly HIV, by administration of a Therapeutic. Such Therapeutics include: MDC proteins and therapeutically and prophylactically effective MDC derivatives and/or analogues, i.e., those derivatives and analogues which prevent or treat HIV infection (e.g., as demonstrated in in vitro assays described infra), as well as nucleic acids encoding such MDC proteins, derivatives and analogues thereof (e.g., for use in gene therapy). Examples of Therapeutics are those chemokines, derivatives and analogues described in Section 5.1 and nucleic acids encoding such proteins. Preferred assays to determine the utility of a specific Therapeutic and whether its administration is indicated for treatment are described in Sections 5.2, 7, 8, 9, and 10.

A preferred embodiment of the invention is directed to methods of using a Therapeutic for treatment and prevention of HIV infection, preferably HIV-1 infection, in a human subject.

Therapeutic compositions of the invention have application in treating and preventing disorders associated with lentiviruses, including, but not limited to, types of HIV, e.g., HIV-1 and HIV-2. A preferred embodiment of the invention relates to methods of using a Therapeutic for treatment or prevention of HIV infection, preferably HIV-1, in a human subject. In the treatment of HIV infection, the Therapeutic of the invention can be used to prevent progression of HIV-1 infection to acquired immune deficiency syndrome AIDS or to AIDS-related complex (ARC) in a human patient, or to treat a human patient with ARC or AIDS.

Therapeutic compositions of the invention also have application in treating and preventing disorders associated with non-human lentiviruses, including, but not limited to, simian immunodeficiency virus.

In a specific embodiment, the therapeutic method of the invention is carried out as monotherapy, i.e., as the only agent provided for treatment or prevention of a lentivirus such as HIV. In another embodiment, the Therapeutic is administered in combination with one or more anti-viral compounds, for example, protease inhibitors (e.g., sequinavir) and/or reverse transcriptase inhibitors (e.g., azidothymidine (AZT), lamioridine (3TC), dideoxyinosine (ddI), dideoxycytidine (ddC)). The anti-viral compound may also be a chemokine, such as RANTES, MIP-1α, MIP-1β or SDF-1, etc. The Therapeutic may also be administered in conjunction with chemotherapy (e.g., treatment with adriamycin, bleomycin, vincristine, vinblastine, doxorubicin and/or Taxol) or other therapies known in the art. In another specific embodiment, the Therapeutic may also be administered in conjunction with an anti-viral drug other than a chemokine and, in a more specific embodiment, the anti-viral drug is other than MDC.

5.3.1. Gene Therapy

In a specific embodiment, nucleic acids comprising a sequence encoding an MDC protein or MDC derivative or analogue that is a protein, effective at inhibiting lentivirus replication and/or infection, in particular HIV replication and/or infection in vitro are administered for treatment or prevention of HIV infection, by way of gene therapy. Gene therapy refers to therapy performed by the administration of a nucleic acid to a subject. In this embodiment of the invention, the nucleic acid produces its encoded protein that mediates a therapeutic effect by preventing or treating lentivirus infection, particularly HIV infection. For example, any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5) :155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid encoding MDC protein, derivative or analogue is part of an expression vector that produces MDC protein, derivative or analogue in a suitable host. In particular, such a nucleic acid has a promoter operably linked to the nucleic acid sequence coding for MDC protein, derivative or analogue, said promoter being inducible or constitutive, and, optionally, tissue-specific. In another particular embodiment, a nucleic acid molecule is used in which the MDC protein, derivative, or analogue sequences and any other desired sequences are flanked by regions that promote homologous recombination at a desired site in the genome, thus providing for intrachromosomal expression of MDC protein, derivative, or analogue (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then administered to the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, J. Biol. Chem. 262:4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al.), WO 93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the nucleic acid sequence encoding a MDC protein, derivative or analogue is used. For example, a retroviral vector can be used (see Miller et al., 1993, Meth. Enzymol. 217:581–599). These retroviral vectors have been modified to delete retroviral sequences that are not necessary for packaging of the viral genome. Retroviral vectors are maintained in infected cells by integration into genomic sites upon cell division. The nucleic acid to be used in gene therapy is cloned into the vector, which facilitates delivery of the gene into a patient. More detail about retroviral vectors can be found in Boesen et al., 1994, *Biotherapy* 6:291–302, which describes the use of a retroviral vector to deliver the drl gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; and Mastrangeli et al., 1993, *J. Clin. Invest.* 91:225–234.

Adeno-associated virus (AAV) has also been proposed for use in gene therapy (Walsh et al., 1993, *Proc. Soc. Exp. Biol. Med.* 204:289–300.) Herpes viruses are other viruses that can also be used.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant blood cells (e.g., hematopoietic stem or progenitor cells) are administered intravenously. Additionally, epithelial cells can be injected, e.g., subcutaneously, or recombinant skin cells (e.g., keratinocytes) may be applied as a skin graft onto the patient. The amount of cells envisioned for use depends on the desired effect, patient state, etc., and can be determined by one skilled in the art.

In an embodiment in which recombinant cells are used in gene therapy, a nucleic acid sequence coding for MDC protein, or therapeutically or prophylactically effective derivative, or analogue is introduced into the cells such that it is expressible by the cells or their progeny, and the recombinant cells are then administered in vivo for therapeutic effect. In a specific embodiment, stem or progenitor cells, preferably hematopoietic stem or progenitor cells, are used. Any stem and/or progenitor cells which can be isolated and maintained in vitro can potentially be used in accordance with this embodiment of the present invention.

5.4. Demonstration of Therapeutic Utility

The Therapeutics of the invention are preferably tested in vitro, and then in vivo for the desired therapeutic or prophylactic activity and/or for toxicity, prior to use in humans. While any in vitro or in vivo assays known in the art may be utilized to test the efficacy of a Therapeutic of the invention, it is preferred that such is determined by applying one or more of the in vitro assays described infra in Sections 5.2, 7, 8, 9, and 10.

5.5. Prophylactic Uses

The Therapeutics of the invention can be administered to prevent lentivirus replication or infection. The prophylactic methods of the invention can be used not only to prevent lentivirus infection, but also as therapeutic methods to prevent post-infection lentivirus replication or further infection that precedes disease development. It is particularly envisioned that administration can follow shortly after an individual engages in behavior that may expose such individual to the viral agent or otherwise render the individual at high risk for developing a lentivirus infection, particularly an immunodeficiency virus infection. Administration of the compositions of the invention may be used as a prophylactic measure in previously uninfected individuals after acute exposure to a lentivirus, particularly an HIV virus. Examples of such prophylactic use of the therapeutic of the invention may include, but is not limited to, prevention of lentivirus transmission, particularly immunodeficiency virus transmission from mother to fetus or infant (e.g., at parturition or through breast milk) and other settings where the likelihood of HIV transmission exists, such as, for example, accidents in health care settings wherein workers are exposed to HIV-containing blood products. Such administration is indicated where the Therapeutic is shown in assays, as described supra, to have utility for treatment or prevention of the transmission of one or more lentivirus strains, preferably HIV.

5.6. Therapeutic/Prophylactic Compositions and Methods of Administering

The invention provides methods of treatment and prevention by administration to a subject in which such treatment or prevention is desired a therapeutically or prophylactically effective amount of a Therapeutic of the invention. The subject is preferably an animal, including, but not limited to, animals such as monkeys, sheep, cows, pigs, horses, chickens, cats, dogs, primates, etc., and is preferably a mammal, and most preferably human. The subject can be a fetus, child, or adult. In a preferred aspect, the Therapeutic is substantially purified.

Formulations and methods of administration that can be employed when the Therapeutic comprises a nucleic acid are described in Sections 5.1 and 5.3.1 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, *J. Biol. Chem.* 262:4429–4432), construction of a Therapeutic nucleic acid as part of a retroviral or other vector, etc. Methods of introduction include, but are not limited to, intradermal, intramuscular, intraperitoneal, intravenous, subcutaneous, intranasal, mucosal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, 1990 *Science* 249:1527–1533; Treat et al., 1989, in Liposomes in the Therapy of Infectious Disease and Cancer, Lopez-Berestein and Fidler (eds.), Liss, New York, pp. 353–365; Lopez-Berestein, ibid., pp. 317–327; see generally ibid.)

In yet another embodiment, the Therapeutic can be delivered in a controlled release system. In one embodiment, a pump may be used (see Langer, 1990, *Science* 249:1527–1533; Sefton 1987, *CRC Crit. Ref. Biomed. Eng.* 14:201; Buchwald et al., 1980; *Surgery* 88:507; Saudek et al., 1989, *N. Engl. J. Med.* 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, N.Y.; Ranger and Peppas, 1983; *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115–138) .Other controlled release systems are discussed in the review by Langer (1990, *Science* 249:1527–1533).

In a specific embodiment where the Therapeutic is a nucleic acid encoding a protein Therapeutic, the nucleic acid can be administered by gene therapy methods as described supra in Section 5.3.1.

The present invention also provides pharmaceutical compositions. Such compositions comprise a therapeutically or prophylactically effective amount of a Therapeutic, and a therapeutically acceptable carrier. In a specific embodiment, the term "therapeutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Therapeutic Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The pharmaceutical compositions of the invention optionally further comprise a therapeutically or prophylactically effective amount of another anti-HIV agent, e.g., AZT, ddI, ddC, 3TC or sequinavir.

The amount of the Therapeutic of the invention which will be effective in the treatment of a particular disorder or condition will depend on the nature of the disorder or condition, and can be determined by standard clinical techniques. In addition, in vivo and/or in vitro assays may optionally be employed to help predict optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1–1000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.7. Methods for Prognosis of Lentivirus Infection Using MDC as Prognostic Indicator MDC expression can be used in methods of detecting lentivirus infection and methods of prognosing disease progression of lentivirus infection, particularly HIV infection.

One method for detection of lentivirus infection, particularly HIV infection in a human subject infected with a lentivirus comprises detecting or measuring changes in the levels of MDC expression by peripheral blood mononuclear cells from the subject, whereby detection or measuring of MDC expression levels at increased levels relative to human subjects uninfected by a lentivirus indicates the presence of lentivirus infection.

In a specific embodiment, such a method for detecting lentivirus infection is utilized when the human subject is asymptomatic with respect to diseases or disorders caused by lentivirus infection.

In a specific embodiment, the method of detecting lentivirus infection utilizes the detection or measurement of MDC protein levels.

In another specific embodiment, the method for detecting lentivirus infection comprises detecting or measuring MDC RNA levels.

In a particular embodiment, a method for predicting the course of lentivirus disease progression in a subject infected with a lentivirus comprises detecting or measuring MDC RNA levels by a method comprising contacting a sample comprising RNA from resting or PHA-activated PBMCs of the subject with a hybridization probe to MDC under conditions conducive to hybridization between the probe and any MDC RNA in the sample, and detecting or measuring any hybridization that occurs.

For example, the expression of MDC in primary PBMCs can be evaluated by northern blot analysis. By way of example, but not limitation, this is done as follows: PBMCs are purified from a donor by banding in Histopaque (Sigma) and harvested after activation for 48 hours in phytohemagglutinin A (PHA; 5 ug/ml) and rIL-1 (10 ng/ml) and recombinant human IL-2 (50U/ml) (Boheringer Mannheim). RNA is isolated by the RNAzol procedure (Tel-Test) and 10 $\mu$g of total cellular RNA is separated by electrophoresis on denaturing formaldehyde-agarose gel, then transferred to a nylon membrane by electroblotting. The blot is hybridized with an MDC-specific probe and washed once with 3×SSC, 0.1% SDS, and twice with 1×SSC, 0.1% SDS at 65° C. for 30 min each wash under stringent conditions as described (Garzino-Demo et al., 1995, *Human Gene Therapy* 6:177). The filter is then exposed for 6 hours at −80° C. using intensifying screens. The probe for northern hybridizations is generated by RT-PCR, using MDC specific primers.

Alterations in expression of MDC in activated PBMCS, in particular $CD8^+$ T lymphocytes, can also be correlated with the progress of the lentivirus, particularly HIV, infection of the patient. In particular, asymptomatic individuals with a lentivirus infection are believed to have increased expression relative to uninfected individuals of MDC by a T cell subset (in particular $CD8^+$ T cells) of PBMCs. Loss of expression by PBMCs from infected individuals indicates progression toward symptomatic lentivirus infection, particularly HIV infection.

One method of prognosing disease progression towards a symptomatic disease state of an individual infected with a lentivirus comprises: detecting or measuring levels of MDC expression by peripheral blood mononuclear cells from the subject, in which a decrease in the level of MDC expression relative to the level of MDC expression at an earlier time period of infection indicates progression of the disease to a symptomatic disease state.

In a specific embodiment of the method of prognosing, the disease is AIDS.

In another specific embodiment of the method of prognosing, the lentivirus is HIV.

In another specific embodiment of the method of prognosing, the peripheral blood mononuclear cells are $CD8^+$ T cells.

In another specific embodiment of the method of prognosing, the detecting or measuring levels of MDC expression is done by detecting or measuring MDC protein levels.

In another specific embodiment, the detecting or measuring of MDC protein levels is done by a method comprising contacting a sample comprising protein from peripheral blood mononuclear cells from an individual (e.g., an infected individual, particularly a seropositive asymptomatic individual) with an antibody to MDC under conditions conducive to immunospecific binding between the antibody and any MDC in the sample; and detecting or measuring any immunospecific binding that occurs.

In another specific embodiment of the method of prognosing, the detecting or measuring levels of MDC expression is done by detecting or measuring MDC RNA levels.

In a specific embodiment, the detecting or measuring of MDC RNA levels is done by a method comprising contacting a sample comprising RNA from peripheral blood mononuclear cells from an individual with a hybridization probe to MDC under conditions conducive to hybridization between the probe and any MDC RNA in the sample; and detecting or measuring any hybridization that occurs.

Alternatively, methods of detection and prognosis of lentivirus, particularly HIV, infection using MDC as a prognostic indicator can use standard immunological techniques to detect the variations in expression of MDC in resting or activated PBMCs.

One method for detecting HIV infection in a subject comprises detecting or measuring MDC levels by a method comprising contacting a sample comprising protein from PBMCs of the subject with an antibody to MDC under conditions conducive to immunospecific binding between the antibody and any MDC in the sample, and detecting or measuring any immunospecific binding that occurs.

The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

6. EXAMPLE: PRODUCTION AND ISOLATION OF MDC

6.1. Production of MDC From CD8$^+$ T Cells

It has been demonstrated that normal CD8$^+$ human T cells immortalized in vitro by human T cell leukemia/lymphotropic virus type I (HTLV-I) are a reproducible source of HIV-1 suppressive activities (Cocchi et al., 1996, Science 270:1811). To produce additional such cell lines, but from HIV-1 infected individuals, CD8$^+$ T cells from HIV-1 infected individuals were transformed by infection with HTLV-I and then cloned by limiting dilution.

CD8$^+$ T cell clones immortalized in vitro were prepared as previously described (Markham et al., 1983, Int. J. Cancer 31:413; Markham et al., 1984, Int. J. Cancer 33:13). Briefly, CD8$^+$ T cells were isolated from HIV-1-infected individuals by positive immunomagnetic selection with anti-CD8 coated beads (Dynal Inc.) and then activated with phytohemagglutinin (PHA) for 48 hrs in complete medium (RPMI 1640 containing 15% fetal calf serum, 10% IL-2, 1% glutamine and 1% penicillin/streptomycin). Cells were washed and exposed to HTLV-I by coculture at a 3:1 ratio with an HTLV-I producing T cell line that was treated by irradiation with 8000 rads for 30 minutes to prevent cell proliferation. Cultures were maintained until clusters of immortalized cells were observed (usually after 2–4 weeks post exposure to HTLV-I). The individual clusters were then transferred into separate culture flasks. Once vigorously growing cells were identified, cells were subjected to single cell cloning by limiting dilution then expanded in complete medium contain 10% IL-2. A CD8$^+$ phenotype of the immortalized cell lines was verified by flow cytometry using anti-CD8 and anti-CD4 antibodies (Becton-Dickinson).

The cell clones were then tested for suppressive activity in an acute infectivity assay with CD8-depleted peripheral blood mononuclear cells (PBMCs). PBMCs from normal donors were activated with PHA for 48 hours and were depleted of CD8$^+$ T cells by negative immunomagnetic selection with anti-CD8-coated magnetic beads (Dynal Inc.). After culturing for 18 hrs in complete medium containing 16 ng/ml recombinant human IL-2 (rIL2; Gemini Biotech), the cells (1×10$^6$) were exposed to 250 doses of fifty percent tissue culture infectious doses (TCID$_{50}$) of the indicated HIV-1 isolates for 3 hrs at 37° C. Cells were then washed with complete medium and placed into 48 well plates (2×10$^5$ cells/well) with a 1:4 dilution of culture supernatant (or the dilution of chemokine indicated in other experiments) in a total volume of 250 μl. Control infections were carried out in complete medium alone. After 48 hours, the medium in each well was replenished with 250 μl of fresh medium containing the same culture supernatant. The level of infection was measured on either day 5 or 6 by HIV-1 p24 ELISA (Organon Teknika). The blocking activity of each supernatant was calculated as percent inhibition of HIV-1 p24 antigen production compared to controls. HIV-1$_{IIIB}$ virus stock was prepared from chronically infected Molt3/HIV-1$_{IIIB}$ cell lines whereas the previously described (R. I. Conner et al., 1993, J. Virol. 67:1772; R. I. Conner et al., 1997, J. Exp. Med. 185:621) primary non-syncytium inducing (NSI) and syncytium inducing (SI) isolates (kindly provided by Dr. Ruth Connor, Aaron Diamond Research Foundation) were propagated in primary PBMCs. All isolates were titered to determine TCID$_{50}$ in PHA-stimulated normal PBMC.

The assays were carried out with primary NSI or SI viruses, or with the T cell line adapted (TCLA) isolate HIV-1$_{IIIB}$. NSI viruses are sensitive to suppression by RANTES, MIP-1α and MIP-1β whereas SI and TCLA viruses are not (Cocchi et al., 1996, Science 270:1811; Dragic et al., 1996, Nature 381:667; Alkhatib et al., 1996, Science 272:1955; Deng et al., 1996, Nature 381:661; Jansson et al., 1996, Proc. Natl. Acad. Sci. USA 93:15382; Conner et al., J. Exp. Med. 185:621). Cell-free supernatants from immortalized CD8$^+$ T cell lines were tested with primary NSI and SI isolates and the TCLA isolate HIV-1$_{IIIB}$. Chemokine levels in the supernatants were assayed by ELISA (R&D Systems). The p24 levels in control assays without test supernatants were 211.56 ng/ml, 290 ng/ml and 300.26 ng/ml for HIV-1$_{IIIB}$, NSI and SI viruses, respectively. The results represent the average of duplicate assays.

As shown in Table 1, the cell clones showed clearly different patterns of suppression when tested with primary NSI and SI isolates or with HIV-1$_{IIIB}$. Notably, two cell clones derived from the same HIV-1-infected individual (F3b Clone 3 and F3b Clone 19) suppressed the primary NSI isolate (NSI 15) and produced high levels of β chemokines. However, only F3b Clone 19 suppressed HIV-1 and the primary SI isolate (SI 06).

TABLE 1

Production of HIV-1 suppressor activity and β-chemokines by HTLV-I-transformed CD8$^+$ T Cells from HIV-1-infected humans.

| Clone | Percent Inhibition of HIV-1 Infection | | | Chemokine (ng/ml) | | |
|---|---|---|---|---|---|---|
| | SI 06 | NSI 15 | IIIB | RANTES | MIP-1α | MIP-1β |
| F3b Clone 3 | 0 | 99.9 | 0 | 137.1 | >70 | >60 |
| F3b Clone 19 | 88.8 | 99.9 | 53.7 | 68.3 | 35 | 21.4 |
| A2a Clone 2 | 12.75 | 74.24 | 56.7 | 115 | 35 | 9.6 |
| B3b Clone 2 | 42.8 | 87.3 | 0 | 83 | 23.8 | 30 |
| B2 Clone 12 | 0 | 94.29 | 0 | 56 | 65 | 8 |
| A2 Clone 5 | 50.07 | 99.8 | 0 | 109.8 | 53 | 25.2 |

F3b Clone 19 was adapted to growth in serum-free medium by the following procedure and used for further studies. F3b Clone 19 cells were grown in complete medium containing rIL-2 (16 ng/ml) at 37° C. in a CO$_2$ incubator. After expanding the culture to 200 ml, the cells were pelleted and resuspended in RPMI medium containing HB101 (Irvine Scientific) supplemented with 16 ng/ml of rIL-2, 1% glutamine and 1% penicillin/streptomycin. The cells were grown to full confluence and the medium harvested by centrifugation at 670×g for 10 minutes.

6.2. Purification and Characterization of MDC

The cell free culture supernatant from F3b Clone 19 was clarified by high speed centrifugation and fractionated by heparin affinity chromatography, taking advantage of the heparin binding characteristics of chemokines (Witt and Lander, 1994, Current Biology 4:394; Proost et al., 1996, Method: A Companion to Methods in Enzymology 10:82). Culture supernatant (1200 ml) from F3b Clone 19, grown to high cell density in serum-free medium supplemented with rIL-2 was clarified by high speed centrifugation (100,000×g for 60 minutes at 4° C.) and applied to a 5 ml HiTrap heparin affinity FPLC column (Pharmacia) equilibrated in 10 mM Tris-HCl, pH 7.6 containing 0.1 M NaCl (column buffer). The column was then washed extensively with column buffer and the bound proteins eluted from the column with 10 mM Tris-HCl, pH 7.6 containing 2.0 M NaCl at a flow rate of 0.5 to 1 ml/minute. Virtually all of the HIV suppressive activity effective against primary NSI and SI isolates and HIV-1$_{IIIB}$ was recovered in the column eluate (data not shown). The heparin affinity column eluate was brought to pH 2.0 by addition of trifluoracetic acid (TFA) and subjected to reversed phase HPLC on a PEEK C-18 column (Waters Instruments) equilibrated in H$_2$O containing 0.1% TFA. Proteins bound to the column were eluted with a 5 minute linear gradient of aqueous acetonitrile (0 to 35%) containing 0.1% TFA. After 10 minutes at 35% acetonitrile, the column was further developed with a 60 minute linear gradient of 35–70% aqueous acetonitrile in TFA. The flow rate was maintained at 0.5 to 1 ml/minute. The fractions obtained were then tested for suppressor activity in the acute infectivity assay using HIV-1$_{IIIB}$. Active fractions were pooled, diluted twofold in H$_2$O ith 0.1% TFA and reapplied to the column. The column was then developed with a 30 minute linear aqueous acetonitrile gradient (0–60%) containing 0.1% TFA at a flow rate of 0.5 to 1 ml/minute. The fractions obtained were assayed as above. ctive fractions were pooled, diluted with H$_2$O/0.1% TFA and fractionated under the same conditions to obtain a single protein peak. The fraction corresponding to the peak and flanking fractions were tested in the infectivity assay to verify that suppressor activity was cofractionated with the protein.

Suppressive activity against HIV-1$_{IIIB}$ in the absence of cytotoxic effects consistently copurif ied with a single protein peak that appeared as a homogeneous 8 kDa band when analyzed by SDS-polyacrylamide gel electrophoresis (FIG. 1). This protein was not reactive in ELISAs for RANTES, MIP-1α or MIP-1β (R&D Systems).

Amino acid analysis of the purified protein was performed with a Beckman 6300 Amino Acid Analyzer (Beckman Instruments). Samples were hydrolyzed for 24 hours at 110° C. in the presence of 6N HCl. Following reconstitution of the samples in loading buffer, the amino acids were analyzed by post-column derivatization using Ninhydrin. N-terminal amino acid microsequencing was performed by automated Edman degradation using a Hewlett-Packard G1005A Protein Sequencing system (Hewlett Packard, Palo Alto, Calif.). The sequencing system was operated using standard reagents, solvents and programs (routine 3.0) as supplied by the manufacturers. The abbreviations used for the amino acid sequences are A; ala; D, asp; E, glu; G, gly; L, leu; M, met; N, asn; R, arg; S, ser; V, val; Y, tyr.

N-terminal amino acid sequence analysis of the purified protein yielded the sequence Tyr-Gly-Ala-Asn-Met-Glu-Asp-Ser-Val-*-*-Arg-Asp-Tyr-Val-Arg-Tyr-Arg-Leu (SEQ ID NO:3); a minor sequence, Pro-Tyr-Gly-Ala-Asn-Met-Glu-Asp-Ser-Val-*-*-Arg (SEQ ID NO:4), was also obtained. After assigning the ambiguous cycles (*) to cysteine residues, a comparison of these sequences with known chemokines revealed identity with the recently described β chemokine, macrophage derived chemokine (MDC) (Godiska et al., 1997, J. Exp. Med. 185:1595). Notably, we did not detect a peptide sequence beginning with an N-terminal glycine, in contrast to the sequence obtained for MDC produced in CHO cells (Godiska et al., 1997, J. Exp. Med. 185:1595–1604; PCT Publication WO 96/40923 dated Dec. 19, 1996). This difference is probably due to a variability in N-terminal processing between cell types. Such variable processing occurs with other chemokines (Lindley et al., 1988, Proc. Natl. Acad. Sci. USA 85:9199; Yoshimura et al., 1989, Mol. Immunol. 26:87; VanDamme et al., 1989, Eur. J. Biochem. 181:337; Herbert et al., 1990, J. Immunol. 145:3033), and is associated with increased potency (Waltz and Baggiolini, 1990, J. Exp. Med. 171:449; VanDamme et al., 1990, Eur. J. Immunol. 20:2113; Clark-Lewis et al., 1991, J. Biol. Chem. 266:23128).

6.3. Suppression of HIV Infection by MDC

A reversed phase HPLC fraction (fraction 27) containing native MDC (nNDC) purified from the F3b Clone 19 cell cultures suppressed the acute infection of CD8-depleted PBMCs by HIV-1$_{IIIB}$ in a concentration dependent manner (FIG. 2). In comparison, flanking fractions (fractions 26 and 28) not containing the protein had no effect. Two preparations of purified nMDC (MDC 1 and MDC 2) were further tested with a variety of primary NSI isolates in the acute infectivity assay with CD8-depleted PBMCs and in infectivity assays with PM1 target cells and the primary macrophage tropic isolate, HIV-1$_{BaL}$.

Two preparations of purified MDC (MDC 1, MDC 2) were tested for suppressor activity with a panel of primary NSI isolates and the TCLA isolate, HIV-1$_{IIIB}$ as described above in Section 6.1. NSI-03 and NSI-15 were obtained sequentially from the same individual. MDC 1 (fraction 27) was tested at 200 ng/ml. MDC 2 was tested at a dilution (1:30) that produced an equivalent concentration of MDC as determined by peak area on the reversed phase HPLC chromatogram versus that obtained for fraction 27. To conserve material, the assays with MDC 1 were performed in 96 well microtiter plate wells in a total volume of 200 μl. The medium was replenished on day 3 by removing 100 μl and replenishing with fresh medium containing MDC 1. The assays were otherwise carried out as described in Section 6.1. above. The two preparations were also tested in an acute infectivity assay with PM1 cells and primary HIV-1$_{BaL}$. PM1 cells (1×10$^5$) were infected with 100 TCID$_{50}$ of virus (propagated in primary macrophages) for 6 hours at 37° C. After washing, cells were treated with purified MDC. On day 2 post infection, virus cultures were fed with fresh medium containing MDC. RANTES (25 ng/ml) purified from the F3b Clone 19 culture supernatant was assayed in parallel as a control. In a separate series of experiments, another preparation of nMDC (MDC 3) was tested at a 1:30 dilution for suppression of primary SIV$_{mac251}$, HIV-1$_{BaL}$ and SI isolates using PBMC target cells as described in Section 6.1. HIV-1$_{IIIB}$ was also tested for comparison. Assays with SIV$_{mac251}$ (propagated and titered in rhesus PBMCs) were modified to use 500 TCID$_{50}$ of virus per 1×10$^6$ cells. Virus replication was determined by p24 ELISA of the culture supernatant on days 4–6. Percent inhibition of infection was calculated based on the level of infection in control assays carried out in the absence of chemokine. The results represent the average of triplicate assays.

As shown in Table 2, the purified nMDC strongly suppressed all of the NSI isolates tested. However, the same preparations did not suppress the infection of PM1 cells by HIV-1$_{BaL}$, although an HPLC fraction containing RANTES produced the expected suppressive effect. In contrast, suppression of HIV-1$_{BaL}$ by nMDC (MDC 3) was observed when PBMCs were used as target cells, indicating that target cell type is an important determinant for activity. Further experiments, as described in Section 6.1, revealed that nMDC was also able to suppress primary SIV$_{mac251}$, SI 06 and another primary SI isolate, 22068-04. Therefore suppression by MDC is not restricted to HIV-1 or to a specific viral phenotype.

TABLE 2

Effects of purified MDC on infection by HIV-1 isolates. NT: Not tested.

| Protein | Percent Inhibition of Infection | | | | |
|---|---|---|---|---|---|
| | NSI 22069-03 | NSI-03 | NSI-15 | IIIB | PM1/Bal |
| MDC 1 | 98.7 | NT | NT | 77.4 | NT |
| MDC 2 | 80.51 | 91.46 | 88.15 | 82.7 | 0 |
| RANTES | NT | NT | NT | 8.5 | 99.50 |
| | SI 22069-04 | SI-06 | SIV$_{mac251}$ | IIIB | PBMC/Bal |
| MDC 3 | 81 | 83 | 66.3 | 68.7 | 54.7 |

To date, the known suppressive chemokines are ligands for receptors used by HIV-1 as coreceptors for virus entry (Feng et al., 1996, *Science* 272:872; Alkhatib et al., 1996, *Science* 272:1955; Dragic et al., 1996, *Nature* 381:997; Choe et al., 1996, *Cell* 85:1135; Doranz et al., 1996, *Cell* 85:1149; Berson et al., 1996, *J. Virol.* 70:6288). It is now clear that the viral phenotype determines which coreceptor is used for entry, and, consequently, the chemokine that blocks infection. Thus, NSI viruses that require CCR5 are suppressed by RANTES, MIP-1α and MIP-1β, SI viruses that use CxCR4 are suppressed by stromal cell derived factor 1 (SDF-1) (Bluel et al., 1996, *Nature* 382:829; Oberlin et al., 1996, *Nature* 382:833), and certain isolates that bind CCR3 are suppressed by eotaxin (He et al., 1997, *Nature* 385:645).

In accordance, the ability of MDC to suppress HIV infection in CD8-depleted PMBCs strongly indicates that a putative MDC receptor serves as an additional HIV-1 coreceptor for certain NSI and SI strains of HIV-1. The capacity to use multiple coreceptors has already been demonstrated for a number of primary isolates (Zhang et al., 1996, *Nature* 383:768; Dittmar et al., 1997, *Nature* 385:495–496; Conner et al., 1997, *J. Exp. Med.* 185:621; Simmons, 1996, *J. Virol.* 70:8355). However, nMDC suppressed the isolates we tested even under conditions where other functional coreceptors were likely to be present on the target cells. The reason for this effect is unclear, however, it is possible that certain coreceptors, including an MDC receptor, act cooperatively in facilitating HIV-1 entry. Analogous findings were obtained with microglia and reporter viruses containing NSI envelope sequences. In this case, microglia expressing both CCR5 and CCR3 were protected from infection by either eotaxin or MIP-1β alone (He et al., 1997, *Nature* 385:645).

The presence of MDC receptors on both macrophages and dendritic cells has important implications for HIV pathogenesis, since these cells are thought to be major vehicles for primary infection (Patterson et al., 1997, *J. Gen. Virol.* 68:1177; Embretson et al., 1993, *Nature* 362:359; Pope et al., 1995, *J. Exp. Med.* 182:2045; Granelli-Piperno et al., 1996, *J. Exp. Med.* 184:2433). MDC is expected to inhibit the infection of dendritic cells, as has been shown for RANTES and SDF-1 (Granelli-Piperno et al., 1996, *J. Exp. Med.* 184:2433). However, it is likely that the MDC receptor is not expressed on certain T cell lines, since MDC was unable to suppress HIV-1$_{BaL}$ infection when PM1 cells were used as targets (Table 2).

6.4. MDC Ability to Raise Cellular Calcium Levels

The ability of nMDC to suppress HIV-1 in the acute infectivity assay suggested that activated CD8-depleted T cells also express the MDC receptor. As recently characterized, MDC induces the migration of monocytes, activated natural killer cells and monocyte-derived dendritic cells (Godiska et al., 1997, *J. Exp. Med.* 185:1595), but its effects on T cells are less well established. Chemokines stimulate a rapid and transient increase in cytosolic calcium levels (Bishoff et al., 1993, *Eur. J. Immunol.* 23:761; Baggiolini et al., 1994, *Advances in Immunol.* 55:97; Bacon et al., 1995, *Science* 269:1727) coincident with the induction of a chemotactic effect. To verify that HIV-1 target cells express an MDC receptor, activated CD8-depleted and unfractionated PBMCs were treated with purified nMDC and analyzed for increases in cytosolic free calcium levels by flow cytometry.

Intracellular calcium was measured by flow cytometry by means of a modification (J. Burns and G. Lewis, manuscript in preparation) of published methods (R. Badolato et al., 1995, *J. Immunol.* 155:4004; R. Greimers et al., 1996, *Cytometry* 23:205). Briefly, unfractionated or CD8-depleted PBMCs (1×10$^6$ cells/ml) prepared as described above and were cultured in the absence of IL-2 for 1 hour. The cells were then washed with RPMI 1640 (Gibco BRL), containing 25 mM Hepes and no phenol red or sodium bicarbonate, and resuspended to a concentration of 2×10$^7$ cells/ml. Aliquots of 1×10$^6$ cells were added to sample tubes, loaded for 20 minutes at 37° C. with fluo-3 (Molecular Probes) reconstituted in a 20% solution of Pluronic F-127 (Molecular Probes) in DMSO 2 $\mu$M and stained with 7-aminoactinomycin D (7-AAD) (Molecular Probes) to discriminate dead cells (I. Schmid et al., 1992, *Cytometry* 13:204). The samples were then washed once as before and resuspended in 1 ml of RPMI 1640 without phenol red and sodium bicarbonate. All samples were kept at 20° C. in the dark until five minutes prior to analysis at which time the sample tube was placed in a 37° C. water bath. The sample was maintained at 37° C. throughout the acquisition of data. Cells were stimulated by addition of test chemokine to a final concentration of 3 nM. Data were acquired with a FACSCalibur (Becton-Dickinson) flow cytometer with excitation at 488 nm. Cells were gated by forward and side scatter properties as well as by 7-AAD exclusion using emission above 650 nm in the FL-3 window. Calcium mobilization was determined by a two parameter density plot of linear emissions collected at 550 nm in the FL-1 window for the gated cell population over time.

As shown in FIGS. 3A–3B, in each case treatment with 3 nM nMDC induced a transient elevation of intracellular calcium. Control experiments with 3 nM SDF-1β or RANTES (R&D Systems) produced the expected strong increase in intracellular calcium in the CD8-depleted T and unfractionated PBMCs, respectively. Coupled with the suppressive effect on a T cell tropic isolate, these results strongly indicate that an MDC receptor is expressed on the target cells used in the infectivity assay.

6.5. Expression of MDC in Primary PBMCs

The expression of MDC in primary PBMCs and in PM1 and HUT 78 T cell lines was evaluated by Northern blot analyses. PBMCs (American Red Cross, Baltimore, Md.) from a healthy donor were purified by banding in Histopaque (Sigma) and harvested either immediately or after activation for 48 hours in phytohemagglutinin A (PHA; 5 μg/ml) and rIL-1 (10 ng/ml). The HUT 78 human T cell line was cultured in the presence (50 U/ml) and absence of IL-2 (Boheringer Mannheim). RNA was isolated by the RNAzol procedure (Tel-Test) and 10 ug of total cellular RNA was electrophoresed on denaturing formaldehyde-agarose gel, then transferred to a nylon membrane by electroblotting. The blot was hybridized with an MDC-specific probe and washed once with 3×SSC, 0.1% SDS, and twice with 1×SSC, 0.1% SDS at 65° C. for 30 min each wash under stringent conditions as described (Garzino-Demo et al., 1995, *Human Gene Therapy* 6:177). The filter was then exposed for 6 hours at −80° C. using intensifying screens. The probe for northern hybridizations was generated by RT-PCR, using MDC specific primers.

As shown in FIG. 4, a strong signal of the expected size (approximately 3 Kb) was detected with RNA from F3b Clone 19 cells, while no signal was detected with PM1 or HUT 78 in the presence or absence of IL-2. Similarly, no signal was detected in primary resting PBMCs from a healthy donor. However, a strong RNA signal was detected in the PBMCs 48 hours after activation with PHA and recombinant human IL-2. These results contrast with experiments conducted elsewhere that did not detect MDC expression in PBMCs (Godiska et al., 1997, *J. Exp. Med.* 185:1595). However, it is likely that MDC expression is variable and reaches high levels under the activation and culture conditions used here.

Northern blot analyses of F3b Clone 3, B3b Clone 2 and A2 Clone 5 cells revealed MDC signals equivalent to what was detected with F3b Clone 19. Thus the ability of F3b Clone 19 culture supernatant to suppress HIV-$1_{IIIB}$ is not due to differential MDC gene expression, and may instead be related to post-translational processes that lead to enhanced secretion or activity of the protein. An additional possibility is that the overall suppressive activity produced by the clones is dictated by a combination of MDC and other molecules that either enhance or inhibit suppressive effects.

7. EXAMPLE: PRIMARY MACROPHAGE/HIV-$1_{BaL}$ CELL FREE INFECTIVITY ASSAY FOR CHEMOKINE SUPPRESSION

The following assay is used to determine the ability of a MDC, derivative or analogue to interfere with the infection or replication of $HIV_{BaL}$. Peripheral blood mononuclear cells (PBMCs) (2×10$^6$) are added to triplicate assay wells of a 48 well culture plate and cultured in 10 ng/ml recombinant human GM-CSF to mature the monocytes into macrophages. After 48 hours the nonadherent cells are washed away and the adherent cells cultured in GM-CSF for an additional 96 hours resulting in mature macrophages. The wells are again washed and then infected with 50 TCID$_{50}$ of HIV-$1_{BaL}$ (available from the NIH AIDS Research and Reference Reagent Program) that has been propagated in primary macrophages in the presence of chemokine, derivative or analogue in a total volume of 200 μl (GM-CSF is no longer present). Each chemokine, derivative or analogue concentration is tested in triplicate wells. Throughout the course of the experiment, controls are maintained in which the cell medium containing the virus does not contain the test chemokine, derivative or analogue. After an overnight (18 hour) incubation each well is washed to remove virus and replenished with fresh medium containing the corresponding amount of chemokine derivative, or analogue. After 48 hours in culture the cells are refed with 200 μl of fresh medium with the corresponding concentration of chemokine, derivative or analogue. Infectivity is determined by commercial HIV-1 p24 antigen capture ELISA on culture well supernatants were collected 5–7 days post-infection (Coulter, Hialeah, Fla.).

Reduced levels of virus in test samples as indicated by reduced levels of p24 in the ELISA relative to the control indicates that the chemokine, derivative, or analogue interferes with the infection or replication of HIV-$1_{BaL}$ in primary macrophage cells at the concentration tested. Preferably, the chemokine derivative or analogue reduces levels of virus, as measured by, for example, p24, by ≧50% relative to control assays carried out in the absence of test compound.

8. EXAMPLE: PRIMARY CD4$^+$ PBMC/ PRIMARY HIV-1 ISOLATE CELL FREE INFECTIVITY ASSAY FOR CHEMOKINE SUPPRESSION

The following assay is used to determine the ability of a chemokine, derivative or analogue to interfere with the infection or replication of a primary HIV-1 isolate in primary CD4$^+$ cells. Target cells can either be peripheral blood mononuclear cells (PBMCs) depleted of CD8$^+$ cells using anti-CD8 immunomagnetic beads or CD4$^+$ PBMCs purified with anti-CD4 immunomagnetic beads. Immunomagnetic bead depletion/purification protocols are carried out according to manufacturer's instructions (Dynal A. S., Norway).

Viruses are isolated according to procedures known in the art. Briefly, isolates are obtained by co-culturing of 1 to 2×10$^6$ PBMCs from HIV-1 infected individuals with phytohemagglutinin (PHA)-stimulated PBMC from two HIV-1 negative blood donors. The cultures are maintained in complete RPMI 1640 medium (Gibco) containing 10% fetal calf serum (FCS), 10–20 ng/ml of rIL2 (R & D Systems, Minneapolis, Minn.), 2 μg/ml polybrene (Sigma, St. Louis, Mo.) and antibiotics. Virus antigen production is measured in supernatants twice weekly using an HIV-1 p24 antigen capture ELISA (Coulter, Hialeah, Fla.). Virus stocks are generated from the p24 antigen capture assay positive supernatants by passaging of the virus isolates once or twice in PHA stimulated blood donor PBMCs. The virus containing supernatants are aliquotted and cryopreserved at −145° C. in liquid nitrogen.

The primary isolates are titered before use so that known doses can be assayed. To determine the 50% tissue culture infectious dose (TCID$_{50}$) of virus stocks, the PBMCs from one normal, healthy donor are activated with PHA and cultured for three days in complete medium of RPMI. The activated PBMCs are thereafter aliquotted in fetal calf serum containing 10% DMSO and cryopreserved at −145° C. (in liquid nitrogen) until use. At the time of virus stock titration and/or chemokine inhibition experiments, the activated PBMCs are thawed and expanded for 2–3 days in complete RPMI 1640 medium. As described in the protocol provided by the manufacturer (Dynal A. S., Norway), CD8$^+$ T cells are depleted from the activated PBMCs using Dynabeads M-450 CD8. CD8$^+$ T-cell depleted PBMCs (1×10$^5$ cells) in complete medium are seeded in microtiter plate wells (96 wells, Nunc, Denmark). Virus stocks are thawed and serially diluted in five fold steps starting from a dilution of 1:2. Each dilution of virus inoculum prepared in complete medium is added to the seeded cell suspension in equal volumes following incubation at 37° C. After one hour incubation, complete RPMI 1640 is added to each well so that total volume per one well is 250 μl. The old medium is removed and new complete medium is added at day three post infection. The harvested culture medium is evaluated for HIV-1 p24 at day seven. The $TCID_{50}$ value is defined as the reciprocal of the virus dilution resulting in 50% positive wells using Reed-Muench calculation or the Spearman-Karber equation.

Phytohemagglutinin (PHA)-activated target cells ($2 \times 10^5$) are incubated for 1–2 hours with 10–50 $TCID_{50}$ of a primary isolate of non-syncytium inducing (NSI) or syncytium-inducing (SI) HIV-1 (which has been obtained from a patient as described in Section 5.2 and propagated only in primary PBMCs) in the presence of chemokines, derivatives or analogues in a total volume of 200–1000 µl.

Controls consist of wells containing the cells, primary HIV-1 isolate, and culture medium in place of chemokine derivative or analogue. The cells are then washed to remove virus and replenished with fresh medium containing the corresponding amount of chemokine. After 48 hours in culture the cells are refed with 200 µl of fresh medium with the corresponding concentration of chemokine. Infectivity is determined by HIV-1 p24 antigen capture ELISA of culture well supernatants were collected 5–7 days post-infection (Coulter, Hialeah, Fla.).

Reduced levels of virus in test samples as indicated by reduced levels of p24 in the ELISA relative to the controls indicate that the chemokine, derivative or analogue interferes with the infection of the primary HIV isolate in primary $CD4^+$ cells.

9. EXAMPLE: ASSAY OF $HIV^+$ PBMCS FOR SUPPRESSION OF HIV IN THE PRESENCE OF MDC

The following assay is used to determine the ability of a chemokine, derivative or analogue to interfere with the ability of a primary HIV-1 isolate from HIV peripheral blood mononuclear cells to replicate and/or infect other $CD4^+$ cells.

$CD4^+$ T cells ($1 \times 10^5$) from uninfected individuals (purified with anti-CD4 immunomagnetic beads) or CD8-depleted PBMCs (cells removed by anti-CD8 immunomagnetic beads) are incubated with $\geq 1000$ $CD4^+$ peripheral blood cells from the infected individual in the presence of different concentrations e.g., 1 ng/ml to 1 µg/ml of test chemokine, derivative or analogue in culture wells. Controls consist of $CD4^+$ infected and non-infected incubations in which chemokine has not been added. For many individuals with advanced infection, $CD4^+$ T cell levels are very low. In these cases, as many cells as possible are incubated with the uninfected $CD4^+$ target cells. The test chemokine concentration is maintained throughout the duration of culture. Culture supernatant samples are removed periodically (every 2–3 days) and tested for virus expression by commercial HIV-1 p24 antigen capture ELISA. Virus is usually detected by day 7.

Reduced levels of virus in the test sample relative to the $CD4^+$ infected controls as indicated by reduced levels of p24 in the ELISA indicate that the chemokine, derivative or analogue interferes with infection or replication of the $HIV^+$ peripheral blood cell HIV-1 isolate in $CD4^+$ cells. Preferably, the chemokine derivative or analogue reduces levels of virus, as measured by, for example, p24, by $\geq 50\%$ relative to control assays carried out in the absence of test compound.

10. EXAMPLE: ASSAY FOR THE EFFECT OF COMPOSITIONS OF THE INVENTION ON CELLULAR PROLIFERATION AND VIABILITY

To rule out the possibility that the antiviral activity of the compositions assayed in Sections 7, 8, and 9 may be due to a negative effect on cellular viability or proliferation, the effect of these compositions on the proliferative response and viability of the target cells is preferably determined for every in vitro test. For example, the effect of the chemokine, derivative, or analogue tested in the primary $CD4^+$ PBMC/primary HIV-$1_{BaL}$ isolate cell-free infectivity assay (Section 13) on the proliferative response of primary $CD4^+$ PBMC may be determined. Peripheral blood mononuclear cells are separated by Ficoll gradient centrifugation and placed in round-bottom 96-well plates ($10^5$ cells/well). $[^3H]$-Thymidine incorporation by stimulated cells is monitored in the presence of concentrations of the compositions corresponding to that used in the in vitro suppression assay (Section 13) and compared with $[^3H]$-Thymidine incorporation in controls that have not been treated with the test composition. The test sample average corrected counts per minute from triplicate cultures and the percent radionucleotide incorporation is compared with that observed for the control. Comparable levels of $[^3H]$-Thymidine incorporation in the test and control samples is indicative that antiviral activity observed in the cell free infectivity assay is not due to the suppression of cellular proliferation.

The effect of the chemokine, derivative, or analogue tested on the viability of primary $CD4^+$ PBMC is determined applying techniques known in the art using trypan blue dye exclusion.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various references are cited herein, the disclosures of hich are incorporated by reference in their entireties.

What is claimed is:

1. A purified protein consisting of amino acids 2–69 of SEQ ID NO:2.

2. A purified protein consisting of amino acids 3–69 of SEQ ID NO:2.

3. A purified protein consisting of the amino acid sequence Tyr-Gly-Ala-Asn-Met-Glu-Asp-Ser-Val-Cys-Cys-Arg-Asp-Tyr-Val-Arg-Tyr-Arg-Leu (amino acids 3–21 of SEQ ID NO:2).

4. A purified protein consisting of the amino acid sequence Pro-Tyr-Gly-Ala-Asn-Met-Glu-Asp-Ser-Val-Cys-Cys-Arg (amino acids 2–14 of SEQ ID NO:2).

5. The protein of claim 3 or 4 which is N-acetylated.

6. The protein of claim 3 or 4 which has a C-terminal amide.

7. The protein of claim 3 or 4 which is N-acetylated and has a C-terminal amide.

8. The purified protein of claim 3 or 4, which inhibits HIV infection and replication in vitro.

9. The protein of claim 1, which is N-acetylated.

10. The protein of claim 2, which is N-acetylated.

11. The protein of claim 1, which has a C-terminal amide.

12. The protein of claim 2, which has a C-terminal amide.

13. The protein of claim 1, which has a C-terminal amide and is N-acetylated.

14. The protein of claim 2, which has a C-terminal amide and is N-acetylated.

15. The purified protein of claim 1, which inhibits HIV infection and replication in vitro.

16. The purified protein of claim 2, which inhibits HIV infection and replication in vitro.

* * * * *